(12) United States Patent
Zhang

(10) Patent No.: US 9,744,528 B2
(45) Date of Patent: Aug. 29, 2017

(54) METALLORGANOCATALYSIS FOR ASYMMETRIC TRANSFORMATIONS

(71) Applicant: Rutgers, The State University Of New Jersey, New Brunswick, NJ (US)

(72) Inventor: Xumu Zhang, Plainsboro, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

(21) Appl. No.: 14/775,159

(22) PCT Filed: Mar. 11, 2014

(86) PCT No.: PCT/US2014/023519
§ 371 (c)(1),
(2) Date: Sep. 11, 2015

(87) PCT Pub. No.: WO2014/164801
PCT Pub. Date: Oct. 9, 2014

(65) Prior Publication Data
US 2016/0023198 A1 Jan. 28, 2016

Related U.S. Application Data

(60) Provisional application No. 61/775,807, filed on Mar. 11, 2013.

(51) Int. Cl.
*C07C 201/12* (2006.01)
*B01J 31/24* (2006.01)
(Continued)

(52) U.S. Cl.
CPC ....... *B01J 31/2409* (2013.01); *B01J 31/2414* (2013.01); *C07B 53/00* (2013.01);
(Continued)

(58) Field of Classification Search
CPC ............ B01J 2531/827; B01J 2531/822; B01J 2531/821; B01J 31/2409; B01J 2531/0205; B01J 2531/842; B01J 2231/645; B01J 2531/824; B01J 2531/16; B01J 2531/0263; B01J 2531/18; B01J 2531/26; B01J 2540/66; B01J 2531/17; B01J 2231/643; B01J 2540/225; B01J 2531/84; B01J 31/2414; B01J 2540/68; B01J 2540/22; C07D 307/38; C07F 17/02; C07F 17/00;
(Continued)

(56) References Cited

U.S. PATENT DOCUMENTS 4,870,208 A 9/1989 Chan et al.
6,133,464 A 10/2000 Pugin et al.
(Continued)

FOREIGN PATENT DOCUMENTS

JP 2002363143 * 12/2002
JP 2007284365 * 11/2007

OTHER PUBLICATIONS

Hayashi; J. Org. Chem. 1988, 53, 113-120.*
Bjelosevic; Journal of Organometallic Chemistry, 2012, 720, 52-59.*
Spencer; Acta Cryst. 2008. E64, m164-m165.*
Bjelosevic; Tetrahedron 2006, 62, 4519-4527.*
He; Tetrahedron: Asymmetry 2001 12, 3213-3216.*
Zanello; Journal of Organometallic Chemistry 2001, 637-639, 800-804.*
Clark; Organometallics, 2000, 19, 994-1002.*
He; Tetrahedron Letters 1998, 39, 411-414.*
Kimmich; Organometallics 1996, 15, 4141-4146.*
Hayashi; Tetrahedron 1992, 48, 1999-2012.*
Pickett; J. Org. Chem. 2003, 68, 2592-2599.*

(Continued)

*Primary Examiner* — Noble Jarrell
*Assistant Examiner* — Daniel Carcanague
(74) *Attorney, Agent, or Firm* — Fox Rothschild LLP

(57) ABSTRACT

A ligand having the structure or its enantiomer; (I) wherein: each one of $R_a$, $R_b$, $R_c$ and $R_d$ is selected from alkyl, cycloalkyl, and aryl; the bridge group is selected from $CH_2NH$; *$CH(CH_3)NH(C^*,R)$; and the organocatalyst is an organic molecule catalyst covalently bound to the bridge group. Also, a catalyst having the structure or its enantiomer: (II) wherein: each one of $R_a$, $R_b$, $R_c$ and $R_d$ is selected from alkyl, cycloalkyl, and aryl; the bridge group is selected from $CH_2NH$; *$CH(CH_3)NH(C^*,R)$; and *$CH(CH_3)NH(C^*,S)$; the organocatalyst is an organic molecule catalyst covalently bound to the bridge group; and M is selected from the group consisting of Rh, Pd, Cu, Ru, Ir, Ag, Au, Zn, Ni, Co, and Fe.

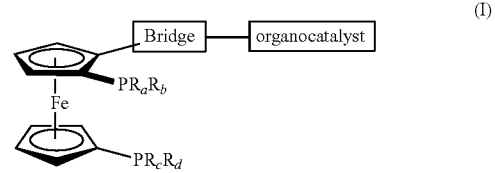

(I)

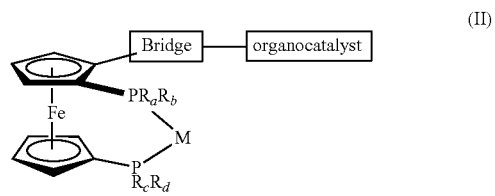

(II)

2 Claims, No Drawings

(51) Int. Cl.
    C07D 307/38    (2006.01)
    C07F 17/02     (2006.01)
    C07C 209/52    (2006.01)
    C07C 213/02    (2006.01)
    C07B 53/00     (2006.01)
    C07F 17/00     (2006.01)

(52) U.S. Cl.
    CPC .......... C07C 201/12 (2013.01); C07C 209/52 (2013.01); C07C 213/02 (2013.01); C07D 307/38 (2013.01); C07F 17/00 (2013.01); C07F 17/02 (2013.01); B01J 2231/643 (2013.01); B01J 2231/645 (2013.01); B01J 2531/0205 (2013.01); B01J 2531/0263 (2013.01); B01J 2531/16 (2013.01); B01J 2531/17 (2013.01); B01J 2531/18 (2013.01); B01J 2531/26 (2013.01); B01J 2531/821 (2013.01); B01J 2531/822 (2013.01); B01J 2531/824 (2013.01); B01J 2531/827 (2013.01); B01J 2531/84 (2013.01); B01J 2531/842 (2013.01); B01J 2540/22 (2013.01); B01J 2540/225 (2013.01); B01J 2540/66 (2013.01); B01J 2540/68 (2013.01)

(58) Field of Classification Search
    CPC ... C07C 201/12; C07C 209/52; C07C 213/02; C07B 53/00

USPC .......................................................... 546/4
    See application file for complete search history.

(56) References Cited

U.S. PATENT DOCUMENTS

| | | |
|---|---|---|
| 2002/0035271 A1 | 3/2002 | Sirges et al. |
| 2005/0124830 A1 | 6/2005 | Hoge et al. |
| 2008/0058522 A1 | 3/2008 | Xiao et al. |
| 2009/0298980 A1 | 12/2009 | Yoshitake et al. |
| 2009/0312561 A1 | 12/2009 | Eastham et al. |
| 2010/0137588 A1 | 6/2010 | Metallinos |
| 2010/0261910 A1 | 10/2010 | Rkyek et al. |
| 2012/0231993 A1 | 9/2012 | Gazic Smilovic et al. |

OTHER PUBLICATIONS

Supplementary European Search Report and Search Opinion in Application 14779902, dated Nov. 3, 2016.*
Hayashi; Bulletin of the Chemical Society of Japan 1980, 53, 1138-1151.*
Gotov; Tetrahedron 56, 2000, 671-675.*
International Search Report and Written Opinion for International Application No. PCT/US2014/023519 dated Aug. 22, 2014.
He, Ren: "Coordination Catalysis and Organometallic Chemistry", Feb. 2002, pp. 94-95.

* cited by examiner

METALLORGANOCATALYSIS FOR ASYMMETRIC TRANSFORMATIONS

CROSS-REFERENCE TO RELATED APPLICATION

This application is the U.S. National Phase of International Patent Application Serial No. PCT/US2014/023519, filed Mar. 11, 2014, which claims the benefit under 35 U.S.C. §119(e) of U.S. Provisional Application Ser. No. 61/775,807, filed Mar. 11, 2013, the disclosures of which are incorporated herein by reference in their entireties.

BACKGROUND

Numerous impressive catalysts have been developed in transition metal catalysis and organocatalysis with unique activation modes. However, the utility of such catalysts is hampered by inherent drawbacks like limited reaction scopes and high catalyst loading. In an effort to improve upon these limitations, the concept of combing transition metal catalysis and organocatalysis has emerged in the last few years. Strategies, including cooperative catalysis, synergistic catalysis, and sequential/relay catalysis, have been established. However, the incompatibility between catalysts, substrates, intermediates and solvents is the potential shortcoming.

SUMMARY

The present document describes a ligand having the structure or its enantiomer:

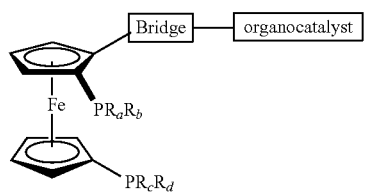

(I)

wherein: each one of $R_a$, $R_b$, $R_c$, and $R_d$ is selected from alkyl, cycloalkyl, and aryl; the bridge group is selected from $CH_2NH$; *$CH(CH_3)NH(C^*,R)$; and *$CH(CH_3)NH(C^*,S)$; and the organocatalyst is an organic molecule catalyst covalently bound to the bridge group. In one embodiment, at least one of $R_a$, $R_b$, $R_c$, and $R_d$ is an aryl moiety selected from phenyl; P—$CH_3$ phenyl; 3,5-di-$CH_3$ phenyl; 3,5-di-t-butyl phenyl; 3,5-di-$CH_3$ phenyl; 2-$CH_3$ phenyl; $C_6F_5$; 2-naphthyl; and 1-naphthyl. In another embodiment, at least one of $R_a$, $R_b$, $R_c$, and $R_d$ is an alkyl moiety selected from t-butyl and i-propyl. In an additional embodiment, at least one of $R_a$, $R_b$, $R_c$, and $R_d$ is a cycloalkyl moiety selected from cyclohexyl and cyclopentyl.

Also provided is a catalyst having the structure or its enantiomer:

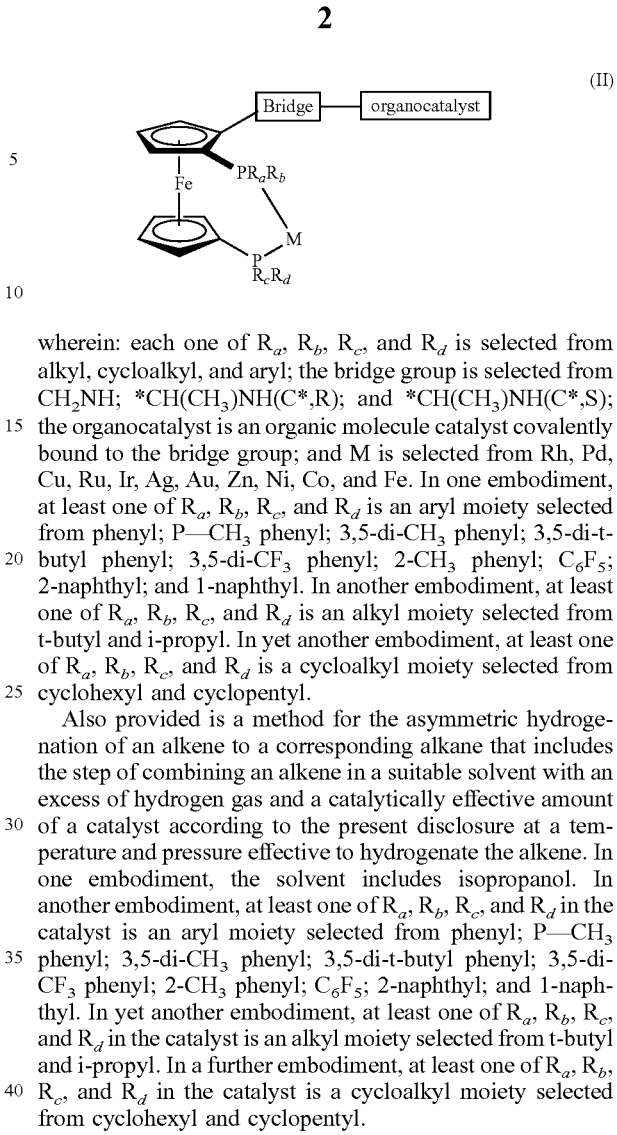

(II)

wherein: each one of $R_a$, $R_b$, $R_c$, and $R_d$ is selected from alkyl, cycloalkyl, and aryl; the bridge group is selected from $CH_2NH$; *$CH(CH_3)NH(C^*,R)$; and *$CH(CH_3)NH(C^*,S)$; the organocatalyst is an organic molecule catalyst covalently bound to the bridge group; and M is selected from Rh, Pd, Cu, Ru, Ir, Ag, Au, Zn, Ni, Co, and Fe. In one embodiment, at least one of $R_a$, $R_b$, $R_c$, and $R_d$ is an aryl moiety selected from phenyl; P—$CH_3$ phenyl; 3,5-di-$CH_3$ phenyl; 3,5-di-t-butyl phenyl; 3,5-di-$CF_3$ phenyl; 2-$CH_3$ phenyl; $C_6F_5$; 2-naphthyl; and 1-naphthyl. In another embodiment, at least one of $R_a$, $R_b$, $R_c$, and $R_d$ is an alkyl moiety selected from t-butyl and i-propyl. In yet another embodiment, at least one of $R_a$, $R_b$, $R_c$, and $R_d$ is a cycloalkyl moiety selected from cyclohexyl and cyclopentyl.

Also provided is a method for the asymmetric hydrogenation of an alkene to a corresponding alkane that includes the step of combining an alkene in a suitable solvent with an excess of hydrogen gas and a catalytically effective amount of a catalyst according to the present disclosure at a temperature and pressure effective to hydrogenate the alkene. In one embodiment, the solvent includes isopropanol. In another embodiment, at least one of $R_a$, $R_b$, $R_c$, and $R_d$ in the catalyst is an aryl moiety selected from phenyl; P—$CH_3$ phenyl; 3,5-di-$CH_3$ phenyl; 3,5-di-t-butyl phenyl; 3,5-di-$CF_3$ phenyl; 2-$CH_3$ phenyl; $C_6F_5$; 2-naphthyl; and 1-naphthyl. In yet another embodiment, at least one of $R_a$, $R_b$, $R_c$, and $R_d$ in the catalyst is an alkyl moiety selected from t-butyl and i-propyl. In a further embodiment, at least one of $R_a$, $R_b$, $R_c$, and $R_d$ in the catalyst is a cycloalkyl moiety selected from cyclohexyl and cyclopentyl.

DETAILED DESCRIPTION

This document describes ligands and catalysts prepared therefrom that provide unexpected improvements in conversion and selectivity in comparison with individual metal catalysts and organocatalysts by covalently bonding chiral bisphosphines with organocatalysts. Metal complexed with bisphosphine is a general catalyst and can lead many metal-catalyzed reactions with high turnovers. Organocatalysts activate substrates and influence selectivities. As used herein, the term "metallorganocatalysis" refers to catalysts and reactions catalyzed by a compound having a metal catalyst portion covalently bound to an organocatalyst portion. The high activity derived from the metal portion and high selectivity from the organocatalyst provide a useful approach in asymmetric catalysis.

As employed above and throughout the disclosure, the following terms, unless otherwise indicated, shall be understood to have the following meanings:

The term "alkyl" refers to the radical of saturated aliphatic groups, including straight-chain alkyl groups and branched-chain alkyl groups. The term "cycloalkyl" refers to a non-aromatic mono or multicyclic ring system of about 3 to 7 carbon atoms. Examples of cycloalkyl groups include cyclopropyl cyclobutyl, cyclopentyl, cyclohexyl and the like.

The term "aryl" refers to any functional group or substituent derived from a simple aromatic ring, be it phenyl, thienyl, indolyl, etc.

Disclosed herein is a ligand having the structure or its enantiomer;

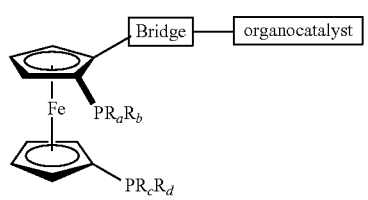

(I)

wherein:

each one of $R_a$, $R_b$, $R_c$, and $R_d$ is selected from alkyl, cycloalkyl, and aryl; the bridge group is selected from CH$_2$NH; *CH(CH$_3$)NH(C*,R); and *CH(CH$_3$)NH(C*, S); and the organocatalyst is an organic molecule catalyst covalently bound to the bridge group.

Each one of $R_a$, $R_b$, $R_c$, and $R_d$ can be the same as or different from any of the other R groups. For example, in one embodiment, all of $R_a$, $R_b$, $R_c$, and $R_d$ are the same aryl group. In another embodiment, each one of $R_a$, $R_b$, $R_c$, and $R_d$ is a different aryl group. In yet another embodiment, $R_a$ and $R_b$ are different aryl groups, while $R_c$ is an alkyl group and $R_d$ is a cycloalkyl group.

Preferred aryl moieties for $R_a$, $R_b$, $R_c$, and $R_d$ include phenyl; P—CH$_3$ phenyl; 3,5-di-CH$_3$ phenyl; 3,5-di-t-butyl phenyl; 3,5-di-CF$_3$ phenyl; 2-CH$_3$ phenyl; C$_6$F$_5$; 2-naphthyl; and 1-naphthyl. Preferred cycloalkyl moieties (e.g. "Cy") for $R_a$, $R_b$, $R_c$, and $R_d$ include cyclohexyl and cyclopentyl. Preferred alkyl moieties for $R_a$, $R_b$, $R_c$, and $R_d$ include t-butyl and i-propyl.

The term "organocatalyst" as used herein includes organic molecules capable of catalyzing a reaction. Suitable organocatalysts contain at least one moiety that can be covalently bound to a bridge group in the ligand of structure (I) or the catalyst of structure (II). Preferred organocatalysts include a thiourea moiety that can be covalently bound to a bridge group. Exemplary organocatalysts include, but are not limited to, the following structures designated as OC1-OC25:

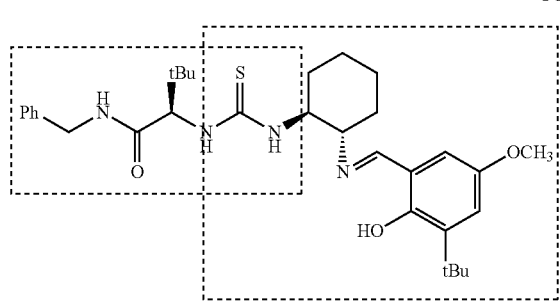

OC1

-continued

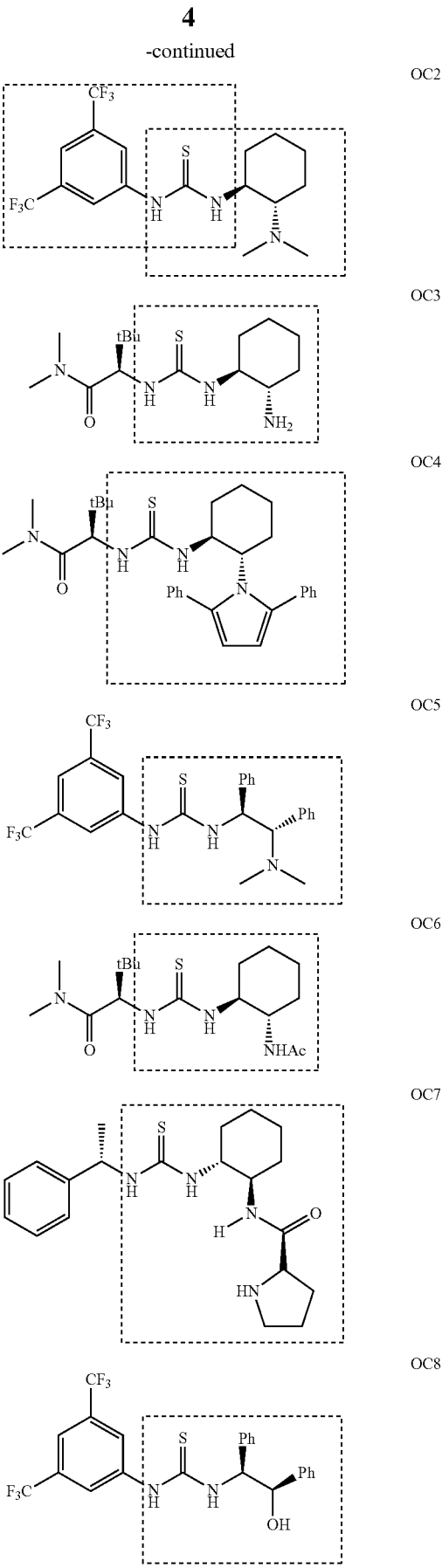

-continued
OC9
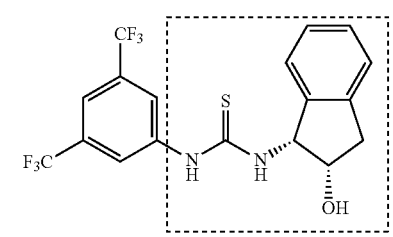
OC10
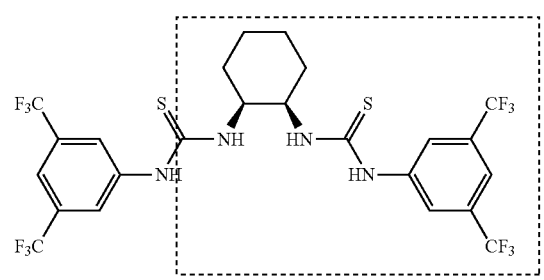
OC11
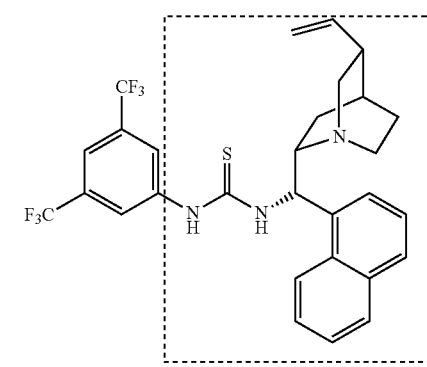
OC12
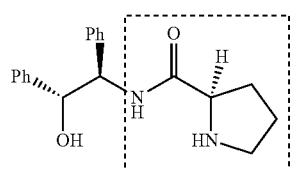
OC13
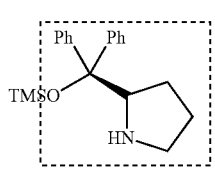
organocatalysis units
OC14
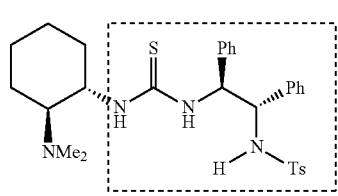
-continued
OC15
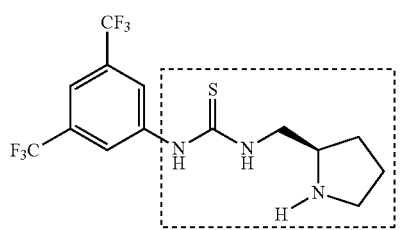
OC16
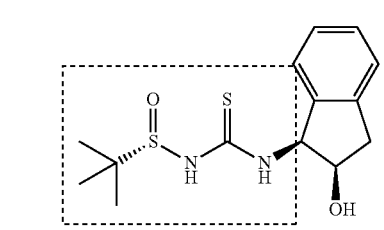
OC17
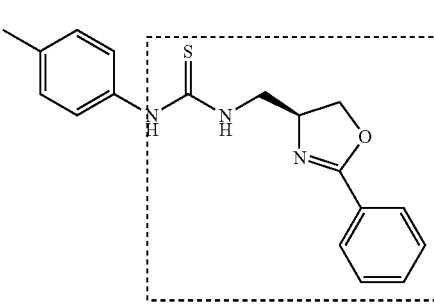
OC18
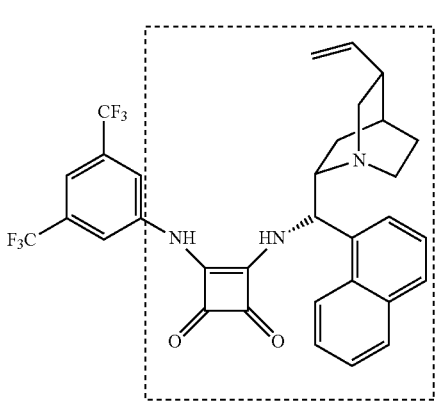
OC19
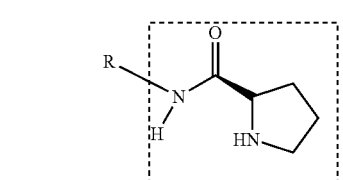
OC20
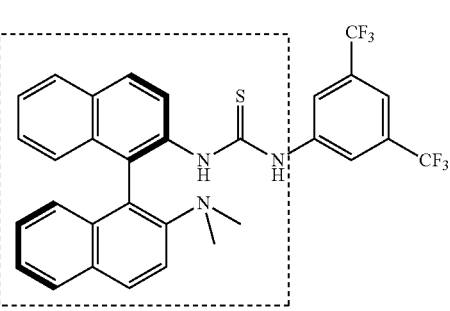

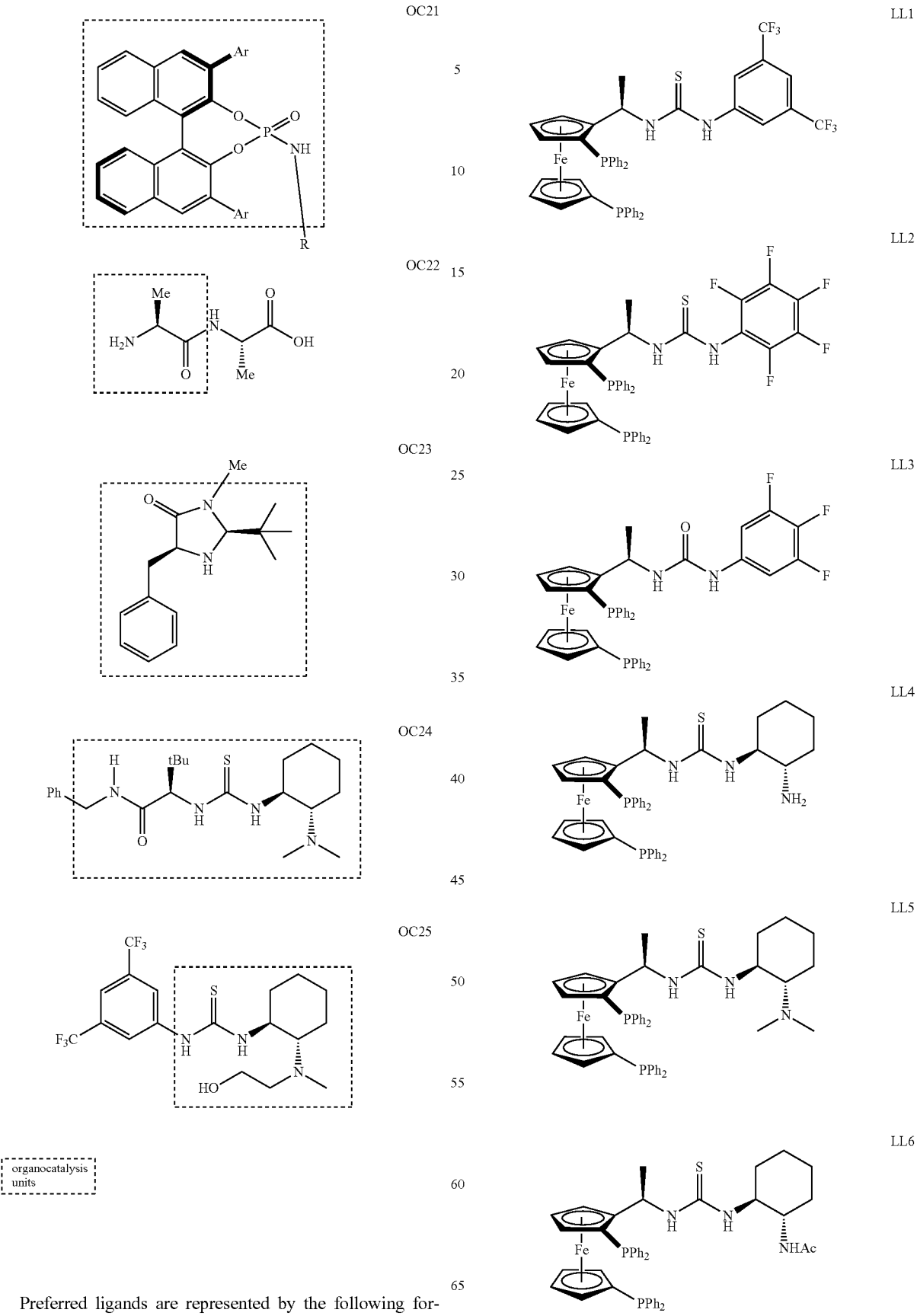
Preferred ligands are represented by the following formulas:

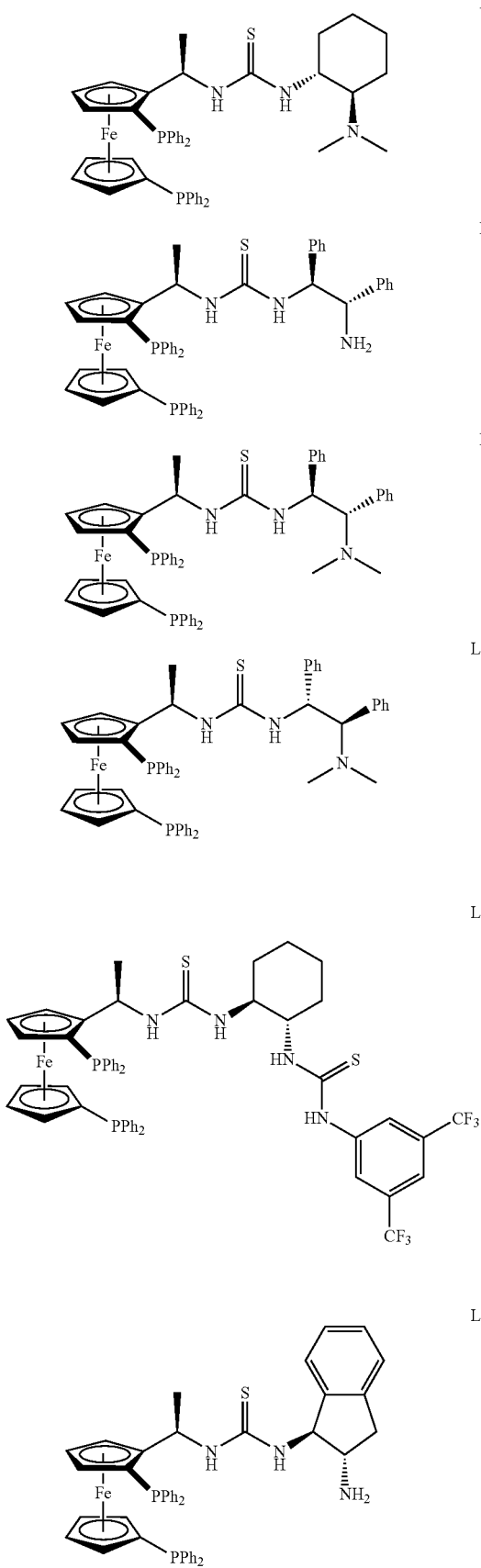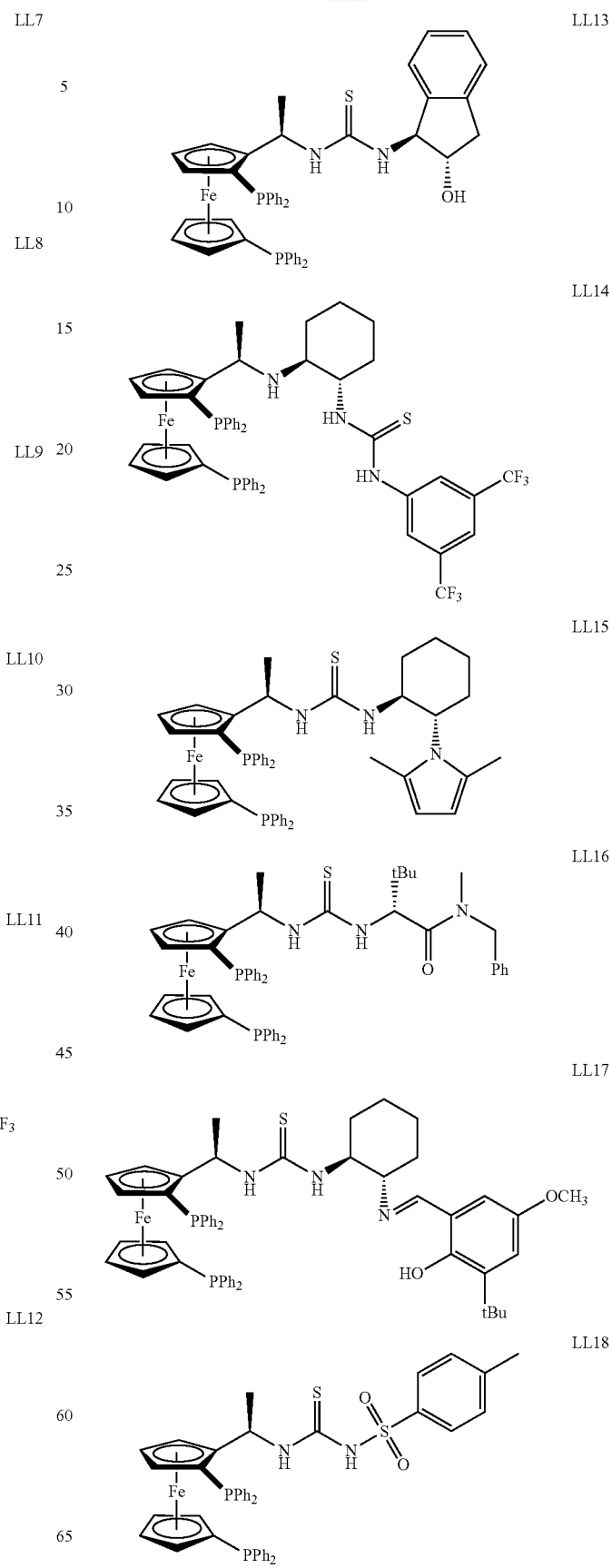

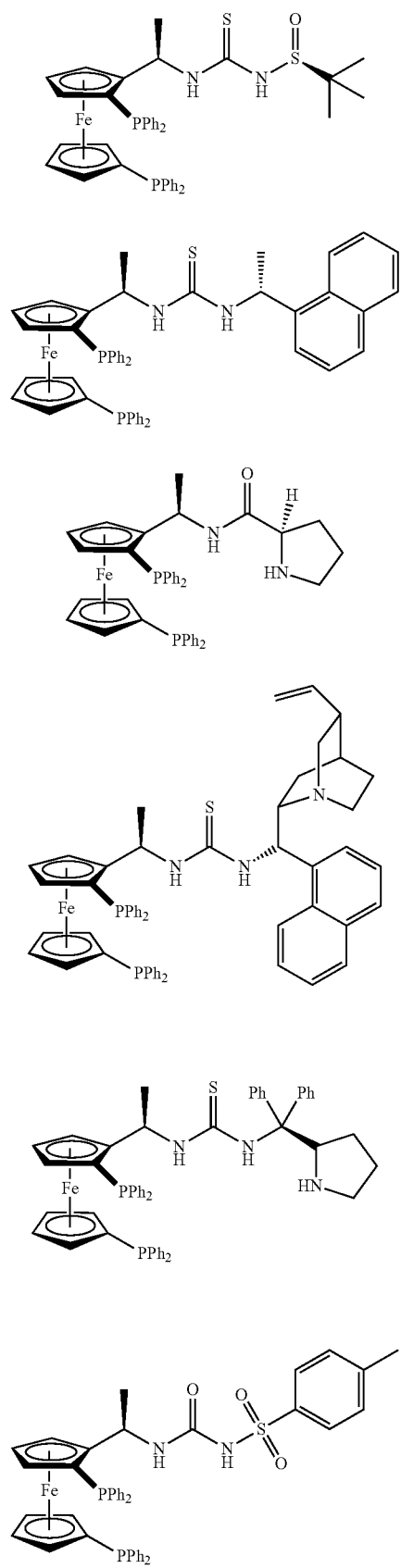
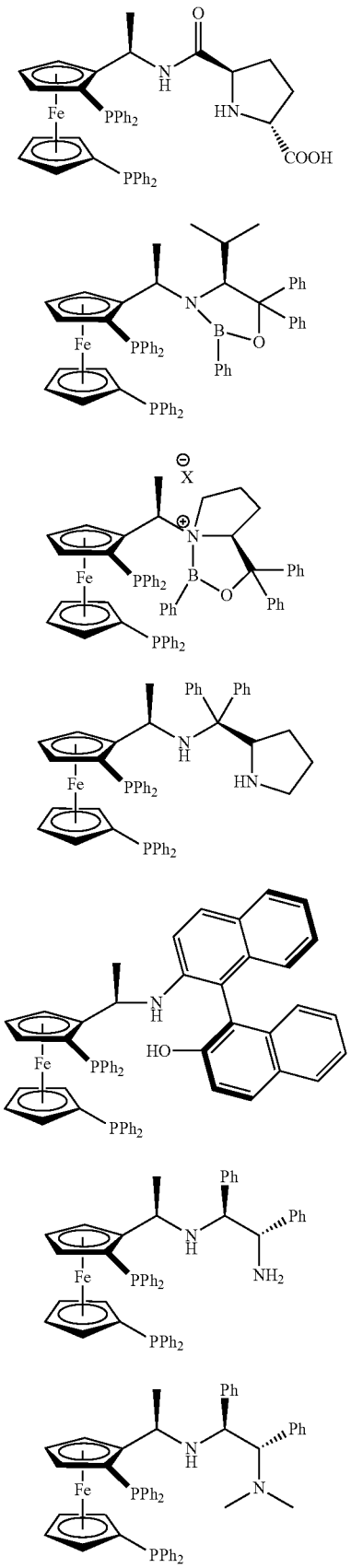

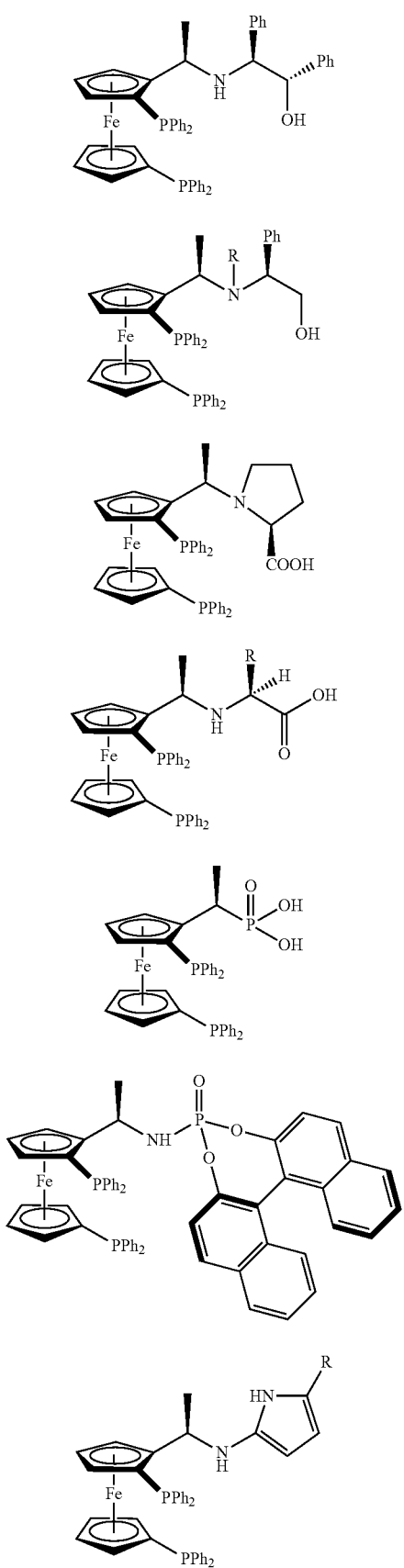
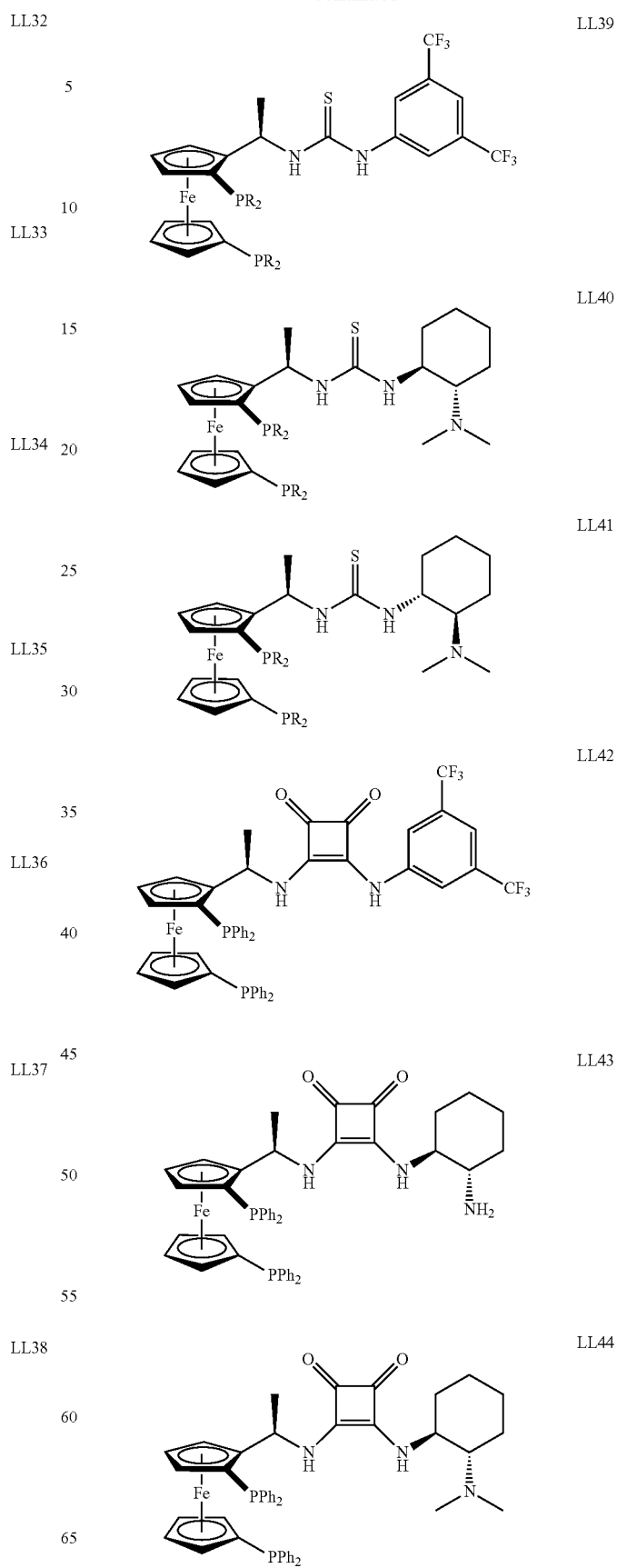

LL45
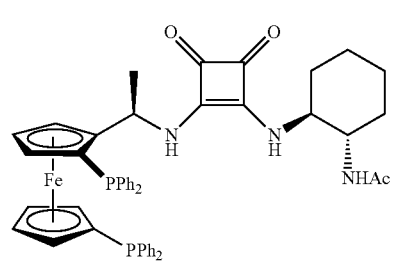
LL46
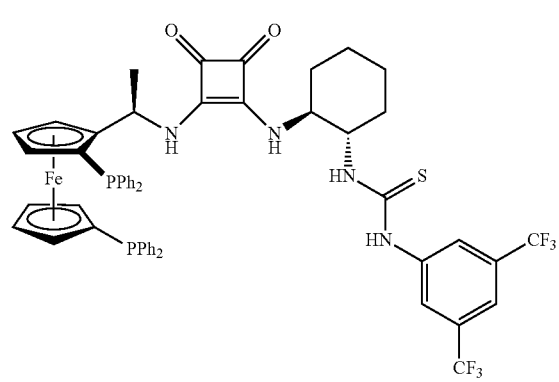
LL47
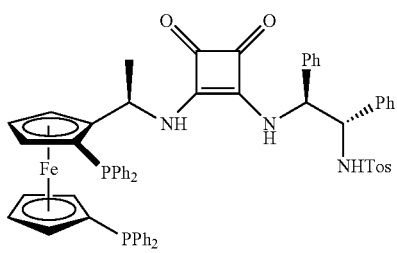
LL48
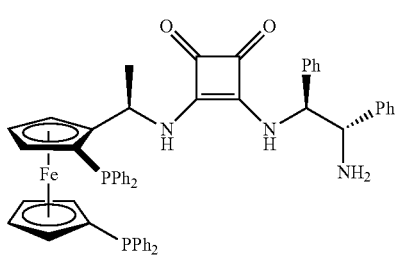
LL49
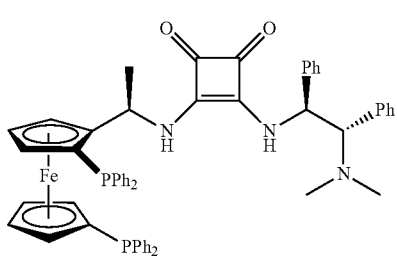
LL50
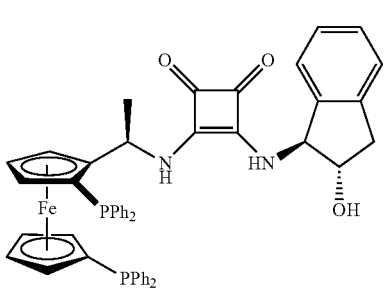
LL51
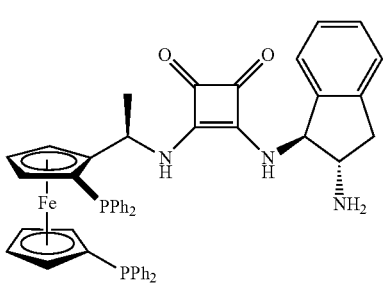
LL52
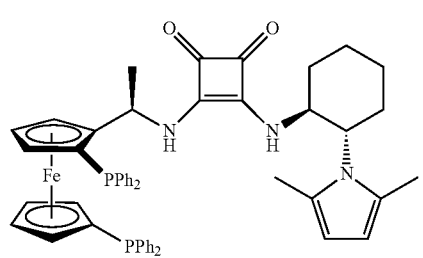
LL53
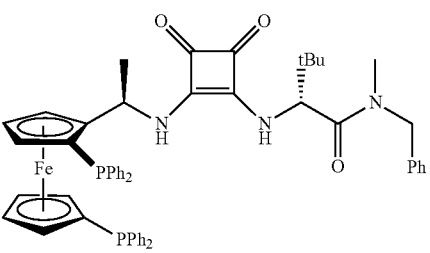
LL54
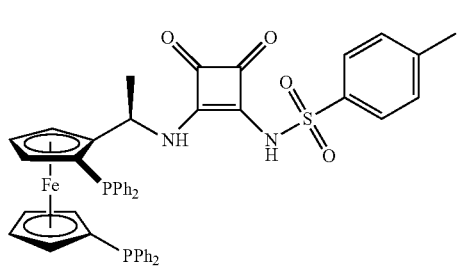

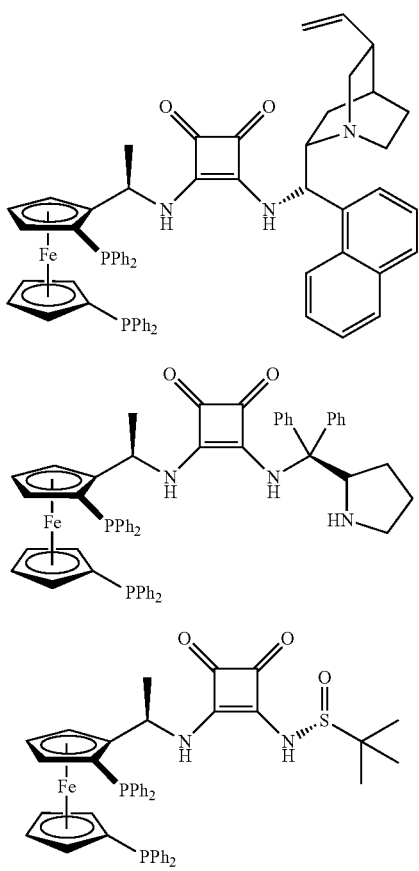

LL55

LL56

LL57

Alternatively, the PPh₂ group in any of the ligands listed above can be PR$_a$R$_b$ or PR$_c$R$_d$, wherein each one of R$_a$, R$_b$, R$_c$, and R$_d$ is selected from alkyl, cycloalkyl, and aryl. Preferred aryl moieties for R include phenyl; P—CH₃ phenyl; 3,5-di-CH₃ phenyl; 3,5-di-t-butyl phenyl; 3,5-di-CF₃ phenyl; 2-CH₃ phenyl; C₆F₅; 2-naphthyl; and 1-naphthyl. Preferred cycloalkyl moieties for R include cyclohexyl and cyclopentyl. Preferred alkyl moieties for R include t-butyl and i-propyl.

Each one of R$_a$, R$_b$, R$_c$, and R$_d$ can be the same as or different from any of the other R groups. For example, in one embodiment, all of R$_a$, R$_b$, R$_c$, and R$_d$ are the same aryl group. In another embodiment, each one of R$_a$, R$_b$, R$_c$, and R$_d$ is a different aryl group. In yet another embodiment, R$_a$ and R$_b$ are different aryl groups, while R$_c$ is an alkyl group and R$_d$ is a cycloalkyl group.

Also disclosed herein is a catalyst having the structure or its enantiomer:

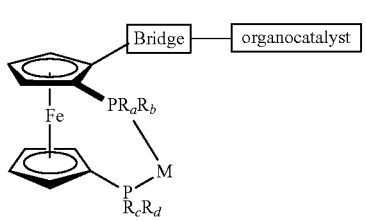

(II)

wherein:

each one of R$_a$, R$_b$, R$_c$, and R$_d$ is selected from alkyl, cycloalkyl, and aryl; the bridge group is selected from CH₂NH; *CH(CH₃)NH(C*,R); and *CH(CH₃)NH(C*,S); and the organocatalyst is an organic molecule catalyst covalently bound to the bridge group. In one embodiment, the bridge group is part of the organocatalyst molecule, for example, a thiourea moiety for dual hydrogen bonding.

Each one of R$_a$, R$_b$, R$_c$, and R$_d$ can be the same as or different from any of the other R groups. For example, in one embodiment, all of R$_a$, R$_b$, R$_c$, and R$_d$ are the same aryl group. In another embodiment, each one of R$_a$, R$_b$, R$_c$, and R$_d$ is a different aryl group. In yet another embodiment, R$_a$ and R$_b$ are different aryl groups, while R$_c$ is an alkyl group and R$_d$ is a cycloalkyl group.

Preferred aryl moieties for R$_a$, R$_b$, R$_c$, and R$_d$ include phenyl; P—CH₃ phenyl; 3,5-di-CH₃ phenyl; 3,5-di-t-butyl phenyl; 3,5-di-CF₃ phenyl; 2-CH₃ phenyl; C₆F₅; 2-naphthyl; and 1-naphthyl. Preferred cycloalkyl moieties for R$_a$, R$_b$, R$_c$, and R$_d$ include cyclohexyl and cyclopentyl. Preferred alkyl moieties for R$_a$, R$_b$, R$_c$, and R$_d$ include t-butyl and i-propyl.

The term "organocatalyst" as used herein includes organic molecules capable of catalyzing a reaction. Suitable organocatalysts contain at least one moiety that can be covalently bound to a bridge group in the ligand of structure (I) or the catalyst of structure (II). Preferred organocatalysts include a thiourea moiety that can be covalently bound to a bridge group. Exemplary organocatalysts include, but are not limited to those listed above.

When a metal catalyst and an organocatalyst are linked through a covalent bond, cooperative interactions such as the following interaction modes offer high activities and selectivities.

Metallorganocatalysis
activation model
substrates actived by metal complexes
and organocatalysis

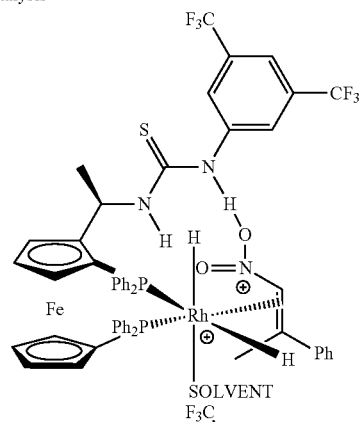

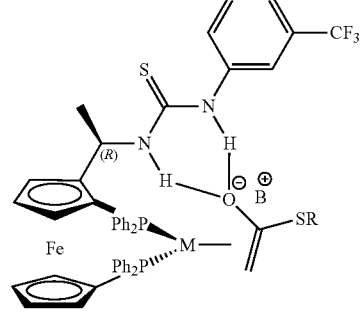

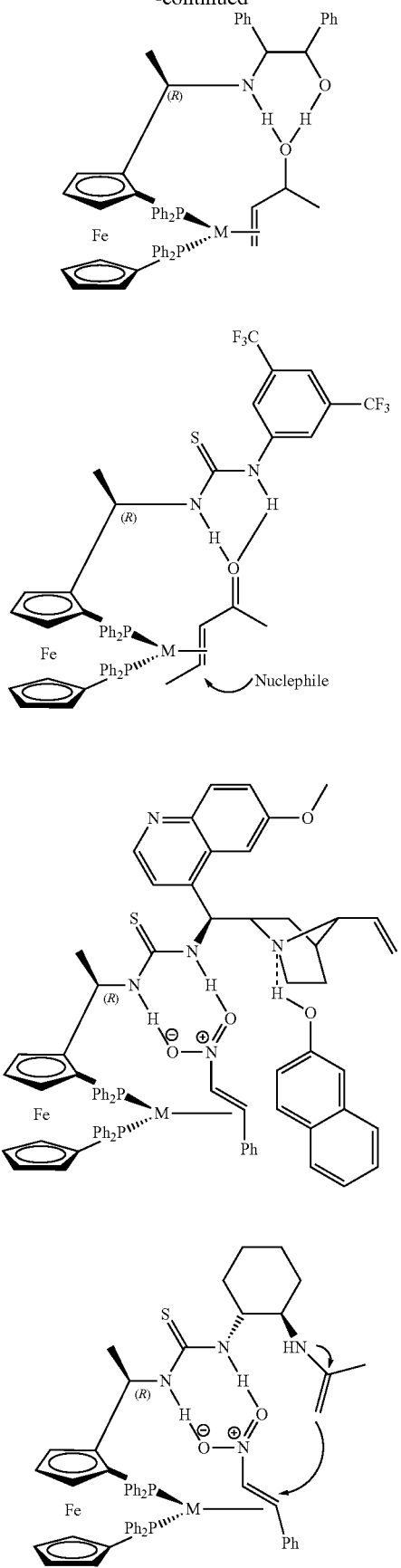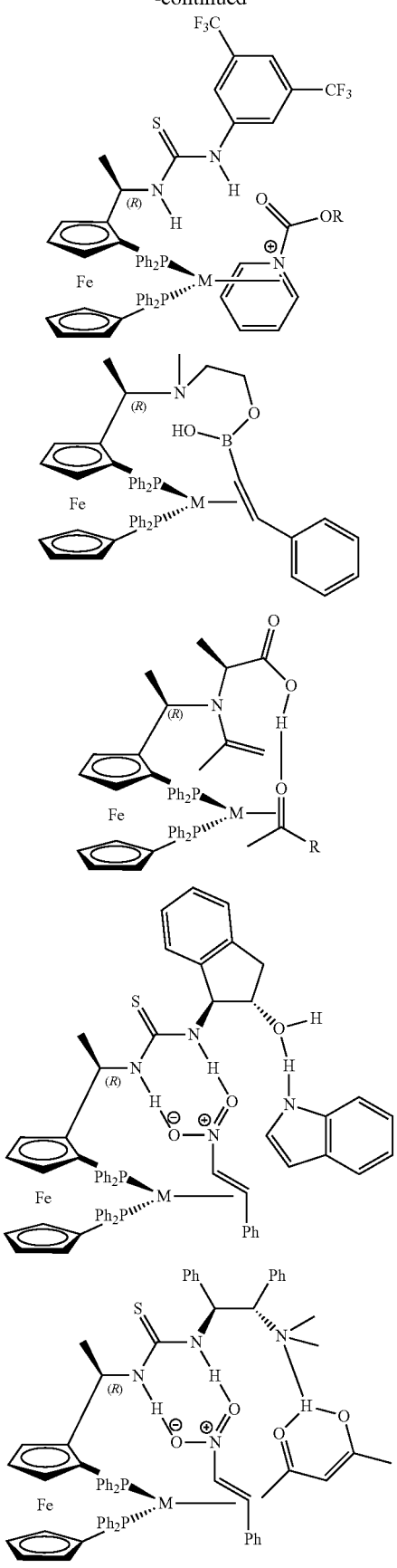

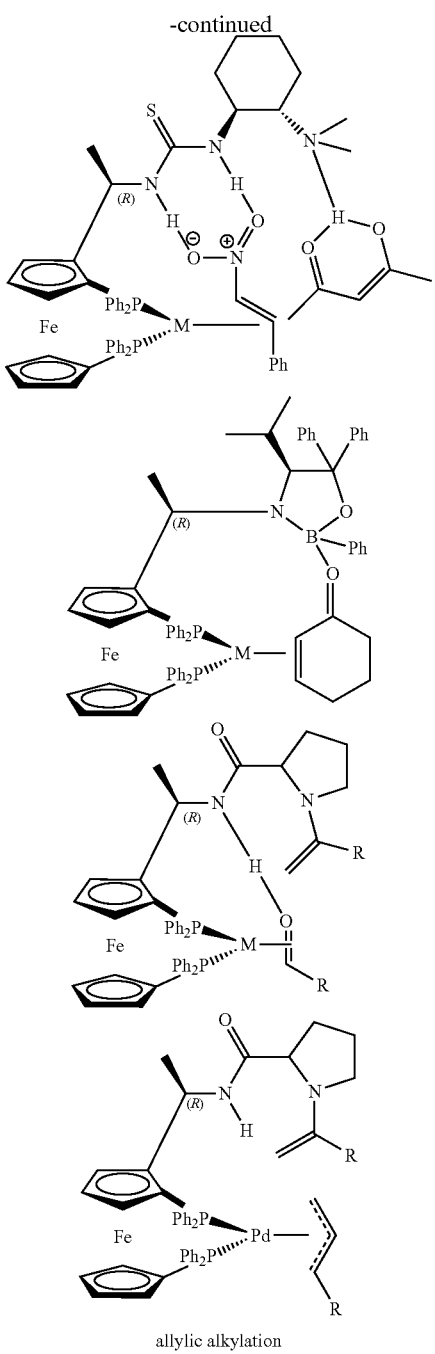

allylic alkylation

Exemplary methods for preparing the ligands and catalysts described herein are discussed in the Examples section.

The catalysts disclosed herein are useful for a wide range of reactions, including, but not limited to, asymmetric hydrogenation, hydroformylation, aldol, Diels-Alder, hetereo Diels-Alder, Mannich, Michael addition, allylic alkylation, alkylation, Friedel-Crafts, ene, Baylis-Hillman, fluorination, and Henry reactions. In one embodiment depicted in the Examples, a method for the asymmetric hydrogenation of an alkene, imine, ketone, or thioketone to a corresponding alkane, amine, alcohol, or thiol is provided, which includes combining an alkene, imine, ketone, or thioketone in a suitable solvent with an excess of hydrogen gas and a catalytically effective amount of a catalyst disclosed herein, and at a temperature and pressure effective to hydrogenate the alkene, imine, ketone or thioketone. In one embodiment, asymmetric hydrogenation of β,β-disubstituted nitroalkenes provided up to >99% conversion and 99% enantioselectivity.

Suitable solvents include, but are not limited to, polar organic solvents. An exemplary polar organic solvent includes, but is not limited to, isopropanol. A catalytically effective amount of a catalyst can be readily determined by one of skill in the art and includes amounts effective to convert an alkene, imine, or ketone to a corresponding chiral alkane, amine, or alcohol.

The following non-limiting examples serves to further illustrate the present invention.

EXAMPLES

Materials and Methods

All reactions dealing with air- or moisture-sensitive compounds were carried out in a dry reaction vessel under a positive pressure of nitrogen or in a nitrogen-filled glovebox. Unless otherwise noted, all reagents and solvents were purchased from commercial suppliers without further purification. Anhydrous solvents were purchased from Sigma-Aldrich and transferred by syringe. Purification of products was carried out by chromatography using silica gel from ACROS (0.06-0.20 mm) and analytical thin layer chromatography (TLC) was carried out using silica gel plates from Merck (GF254). [Rh(COD)Cl]$_2$, [Rh(COD)$_2$]BF$_4$ and [Rh(COD)$_2$]SbF$_6$ were purchased from Heraeus. The HPLC solvents were purchase from Alfa (n-Hexane) and Sigma-Aldrich (2-Propanol).

$^1$H NMR, $^{13}$C NMR and $^{31}$P NMR spectra were recorded on a Bruker Avance (400 MHz) spectrometer with CDCl$_3$ as the solvent and tetramethylsilane (TMS) as the internal standard. Chemical shifts are reported in parts per million (ppm, δ scale) downfield from TMS at 0.00 ppm and referenced to the CDCl$_3$ at 7.26 ppm (for $^1$H NMR) or 77.0 ppm (for deuterochloroform). Data are reported as: multiplicity (s=singlet, d=doublet, t=triplet, q=quartet, m=multiplet), coupling constant in hertz (Hz) and signal area integration in natural numbers. $^{13}$C NMR and $^{31}$P NMR analyses were run with decoupling.

Enantiomeric excess values ("ee") were determined by Daicel chiral column on an Agilent 1200 Series HPLC instrument or an Agilent 7980 Series GC instrument. New compounds were further characterized by high resolution mass spectra (HRMS) on a Waters Q-T of Ultima mass spectrometer with an electrospray ionization source (University of Illinois, SCS, Mass Spectrometry Lab). Optical rotations [α]$_D$ were measured on a PERKINELMER polarimeter 343 instrument.

All (E)-β,β-disubstituted nitroalkenes were prepared according the literature. (Li, S., et al., *Angew. Chem. Int. Ed.* 2012, 51, 8573-8576). All N—H imines were prepared according to the literature. (Hou, G., et al., *J. Am. Chem. Soc.* 2009, 131, 9882-9883.) The absolute configuration of products were determined by comparison of analytical data with the literature (HPLC spectra, optical rotation). The absolute configuration of others were assigned by analogy.

Example 1—Synthesis of Ligands
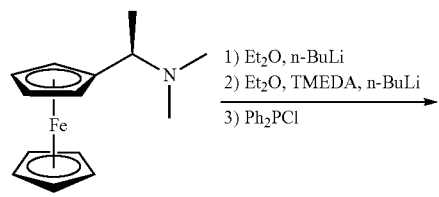
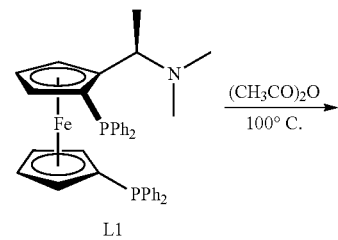
L1
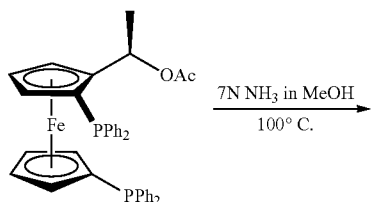
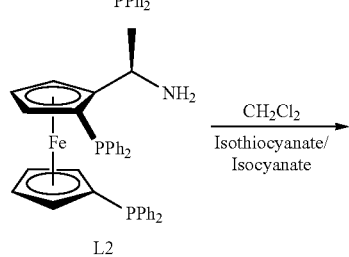
L2
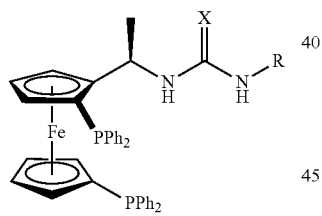
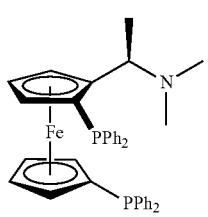
L1
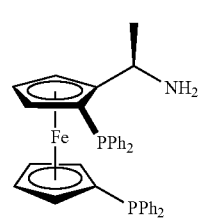
L2
-continued
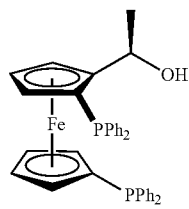
L3
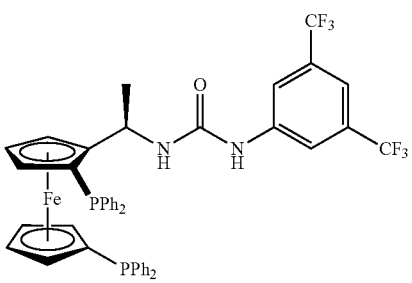
L4
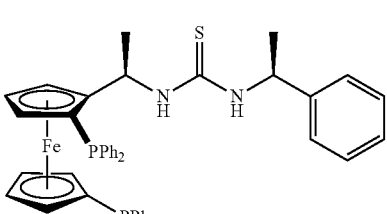
L5
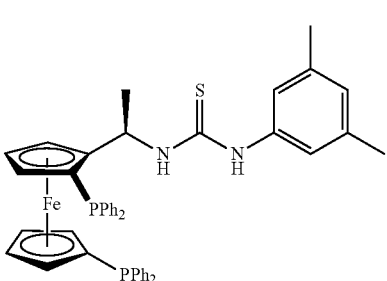
L6
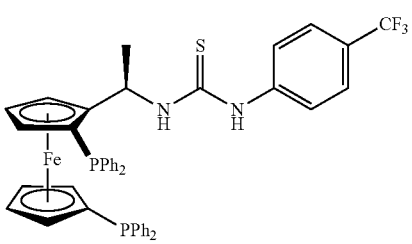
L7
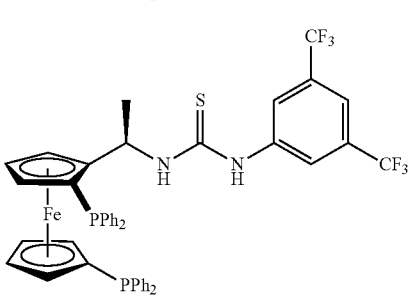
L8
Ligands L1-L3 were prepared according the according the literature (Hayashi, T., et al., *Bull. Chem. Soc. Jpn.* 1980, 53, 1138-1151) with a slight modification: column chromatography was performed using silica gel (hexane/ethyl acetate for L1 and dichloromethane/methanol for L2) instead of alumina (hexane/benzene for L1 and ether/ethyl acetate for L2). All the spectral data are consistent with the literature values.

Under an argon atmosphere, 3,5-bis(trifluoromethyl)phenyl isothiocyanate (1.1 mmol) was added to a solution of L2 (1.0 mmol) in dry DCM (1.0 ml). After the reaction mixture was stirred overnight, the reaction mixture was concentrated in vacuo. The residue was purified by flash column chromatography on silica gel (hexane/ethyl acetate=9/1 as eluant) gave L8 as yellow solid (640 mg, 74%). L8 was characterized as follows:

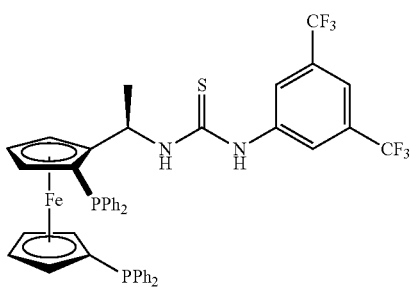

L8

$^1$H NMR (400 MHz, CDCl$_3$) δ 7.69 (s, 3H), 7.33-7.12 (m, 19H), 7.11-7.01 (m, 3H), 5.53 (s, 1H), 4.47 (d, J=7.2 Hz, 2H), 4.28 (s, 1H), 4.18 (t, J=2.3 Hz, 1H), 3.96 (s, 1H), 3.56 (s, 1H), 3.45 (s, 1H), 1.42 (d, J=6.6 Hz, 1H).
$^{13}$C NMR (100 MHz, CDCl$_3$) δ 178.37 (s), 139.18 (s), 138.94 (d, J=9.6 Hz), 138.82 (d, J=6.3 Hz), 138.04 (d, J=9.4 Hz), 135.55 (d, J=5.0 Hz), 134.68 (d, J=21.2 Hz), 133.71 (d, J=20.1 Hz), 133.01 (d, J=19.2 Hz), 132.20 (d, J=17.8 Hz), 129.58 (s), 128.97-127.94 (m), 124.48 (s), 124.31 (s), 121.60 (s), 119.16 (s), 95.36 (d, J=24.1 Hz), 77.63 (d, J=8.5 Hz), 75.34 (d, J=20.4 Hz), 74.16 (d, J=9.1 Hz), 73.84 (d, J=4.9 Hz), 73.37 (d, J=8.5 Hz), 73.10-72.50 (m), 71.97 (d, J=2.6 Hz), 50.87 (s), 21.86 (s).
$^{31}$P NMR (162 MHz, CDCl$_3$) δ −17.81 (s), −25.08 (s).
$[α]_D^{25}$=237.3° (c=0.30, CHCl$_3$)
HRMS (ESI): [M+H$^+$] Calc. 869.1406. found 869.1401.

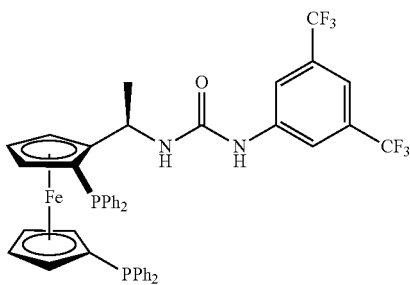

L4

$^1$H NMR (400 MHz, CDCl$_3$) δ 7.54 (s, 2H), 7.42-7.38 (m, 3H), 7.34-7.14 (m, 18H), 5.13 (s, 2H), 5.13-5.07 (m, 1H), 4.48 (d, J=1.7 Hz, 2H), 4.37 (d, J=7.4 Hz, 2H), 4.19 (d, J=8.1 Hz, 2H), 4.14 (t, J=2.3 Hz, 1H), 3.65 (s, 1H), 3.57 (s, 1H), 1.46 (d, J=6.7 Hz, 3H).
$^{13}$C NMR (100 MHz, CDCl$_3$) δ 152.34 (s), 140.51 (s), 140.39 (s), 138.90 (d, J=9.7 Hz), 138.14 (d, J=9.4 Hz), 135.89 (d, J=8.1 Hz), 134.92 (d, J=21.2 Hz), 133.60 (d, J=20.0 Hz), 133.06 (d, J=19.2 Hz), 132.44 (d, J=18.8 Hz), 131.76 (d, J=33.2 Hz), 129.39 (s), 128.72 (s), 128.62-127.96 (m), 124.55 (s), 121.84 (s), 118.11 (d, J=3.1 Hz), 115.21 (s), 95.11 (d, J=23.6 Hz), 77.19 (s), 75.78 (d, J=10.3 Hz), 75.36 (d, J=19.6 Hz), 74.33 (d, J=3.0 Hz), 73.42-71.18 (m), 73.11 (d, J=4.5 Hz), 71.67 (d, J=2.2 Hz), 71.24 (d, J=1.9 Hz), 45.48 (d, J=7.1 Hz), 20.65 (s).
HRMS (ESI): [M+H$^+$] Calc. 853.1635. found 853.1644.
$[α]_D^{25}$=262.1° (c=0.33, CHCl$_3$).

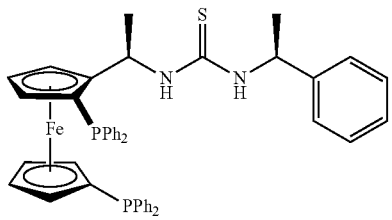

L5

$^1$H NMR (400 MHz, CDCl$_3$) δ 7.44 (t, J=7.2 Hz, 2H), 7.40-7.11 (m, 24H), 6.00 (s, 2H), 5.46 (s, 1H), 4.60 (s, 1H), 4.57-3.52 (m, 4H), 3.56 (d, J=10.8 Hz, 2H), 1.35 (d, J=6.6 Hz, 3H), 1.04 (d, J=6.2 Hz, 3H).
$^{13}$C NMR (100 MHz, CDCl$_3$) δ 178.66 (s), 141.83 (s), 139.05 (d, J=2.9 Hz), 138.97 (s), 138.23 (d, J=9.6 Hz), 136.13 (d, J=7.2 Hz), 134.71 (d, J=21.0 Hz), 133.62 (d, J=20.1 Hz), 132.98 (d, J=19.2 Hz), 132.55 (d, J=18.6 Hz), 129.29 (s), 128.98-127.45 (m), 125.65 (s), 95.44 (d, J=23.6 Hz), 77.17 (d, J=8.1 Hz), 75.25 (d, J=19.9 Hz), 74.80 (d, J=10.3 Hz), 74.08 (d, J=4.5 Hz), 73.25 (d, J=9.0 Hz), 73.13 (s), 72.72 (d, J=4.3 Hz), 72.41 (s), 71.50 (d, J=2.6 Hz), 52.79 (s), 50.51 (s), 23.82 (s), 21.45 (s).
$^{31}$P NMR (162 MHz, CDCl$_3$) δ −17.66 (s), −25.81 (s).
HRMS (ESI): [M+H$^+$] Calc. 761.1972. found 761.1972.
$[α]_D^{25}$=343.5° (c=0.21, CHCl$_3$).

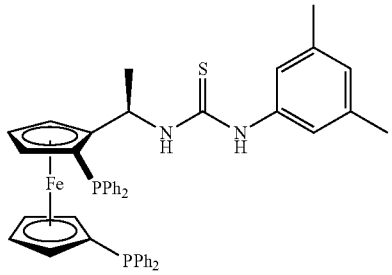

L6

$^1$H NMR (400 MHz, CDCl$_3$) δ 8.21 (t, J=9.1 Hz, 1H), 7.59 (s, 1H), 7.25-6.92 (m, 23H), 5.51-5.41 (m, 1H), 4.43-4.38 (m, 2H), 4.29 (s, 1H), 4.17 (s, 1H), 3.70 (s, 1H), 3.40 (s, 1H), 3.09 (s, 1H), 2.42 (s, 6H), 1.24 (d, J=6.9 Hz, 3H).
$^{13}$C NMR (100 MHz, CDCl$_3$) δ 178.51 (s), 140.22 (s), 139.32 (d, J=9.9 Hz), 138.56 (d, J=5.4 Hz), 138.03 (d, J=9.7 Hz), 135.93 (s), 134.64 (d, J=21.2 Hz), 133.84 (d, J=20.4 Hz), 132.76 (d, J=18.9 Hz), 132.08 (d, J=17.5 Hz), 129.27 (d, J=17.7 Hz), 128.67 (s), 128.29-127.92 (m), 96.88 (d, J=24.1 Hz), 75.39 (d, J=22.6 Hz), 73.95 (d, J=5.3 Hz), 73.65 (d, J=5.6 Hz), 72.98 (d, J=6.8 Hz), 72.81 (s), 72.56 (d, J=3.7 Hz), 72.16 (d, J=3.6 Hz), 51.84 (s), 24.43 (s), 21.48 (s).
$^{31}$P NMR (162 MHz, CDCl$_3$) δ −17.61 (s), −25.96 (s).
HRMS (ESI): [M+H$^+$] Calc. 761.1972. found 761.1964.
$[α]_D^{25}$=−219.9° (c=0.22, CHCl$_3$)

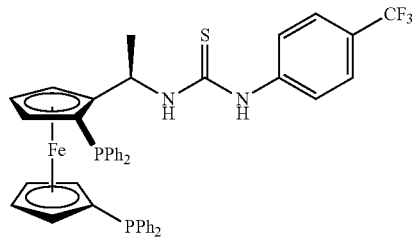
L7

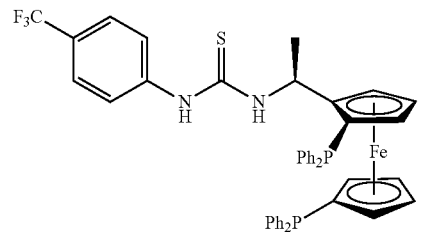
L12

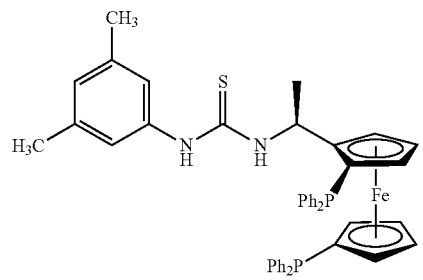
L13

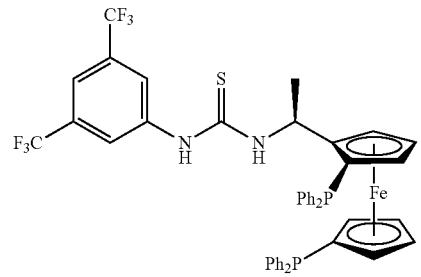
L14

<sup></sup>¹H NMR (400 MHz, CDCl₃) δ 8.22 (s, 1H), 7.73 (d, J=8.4 Hz, 2H), 7.71-7.64 (m, 1H), 7.35-7.13 (m, 18H), 7.08-7.02 (m, 4H), 5.56-5.46 (m, 1H), 4.45 (s, 1H), 4.32 (s, 1H), 4.25 (s, 1H), 4.17 (t, J=2.4 Hz, 1H), 3.72 (s, 1H), 3.50 (s, 1H), 3.26 (s, 1H), 1.33 (d, J=6.8 Hz, 1H).

$^{13}$C NMR (100 MHz, CDCl₃) δ 178.11 (s), 139.79 (s), 139.14 (d, J=9.8 Hz), 138.63 (d, J=5.5 Hz), 137.96 (d, J=9.4 Hz), 135.58 (d, J=4.5 Hz), 134.68 (d, J=21.2 Hz), 133.81 (d, J=20.3 Hz), 132.83 (d, J=18.9 Hz), 132.22 (s), 130.27-129.77 (m), 128.78 (s), 128.66-128.01 (m), 127.27 (d, J=3.4 Hz), 125.01 (s), 95.87 (d, J=24.2 Hz), 77.59 (d, J=8.6 Hz), 75.42 (d, J=22.0 Hz), 73.63 (d, J=5.2 Hz), 73.14 (d, J=7.2 Hz), 72.83 (s), 72.08 (d, J=3.0 Hz), 51.60 (s), 23.10 (s).

$^{31}$P NMR (162 MHz, CDCl₃) δ −17.85 (s), −26.34 (s).

HRMS (ESI): [M+H]⁺ Calc. 801.1532. found 801.1538.

$[\alpha]_D^{25}$=−239.5° (c=0.30, CHCl₃)

Ligands L9-L14 were prepared according the according the literature (Zhao, Q., et al., *Org. Lett.* 2013, 15, 4014-4017).

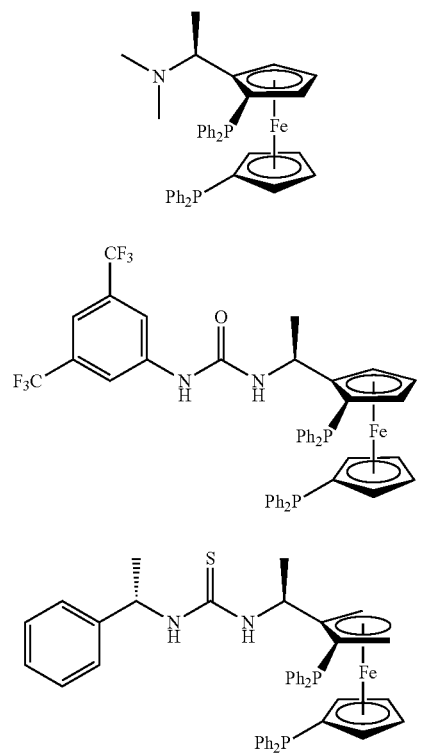

L9

L10

L11

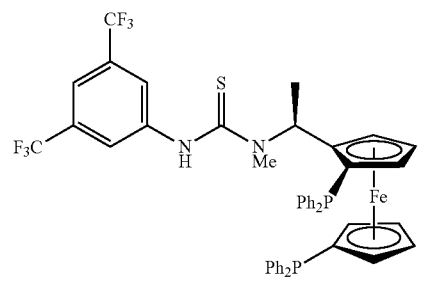
L15

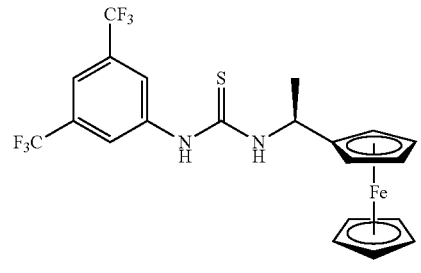
L16

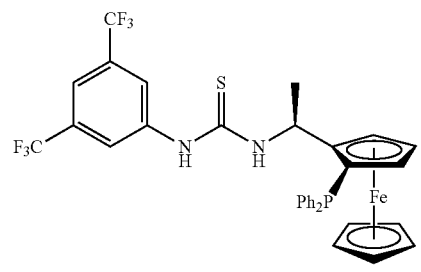
L17

Ligands L15-L17 were synthesized as follows:

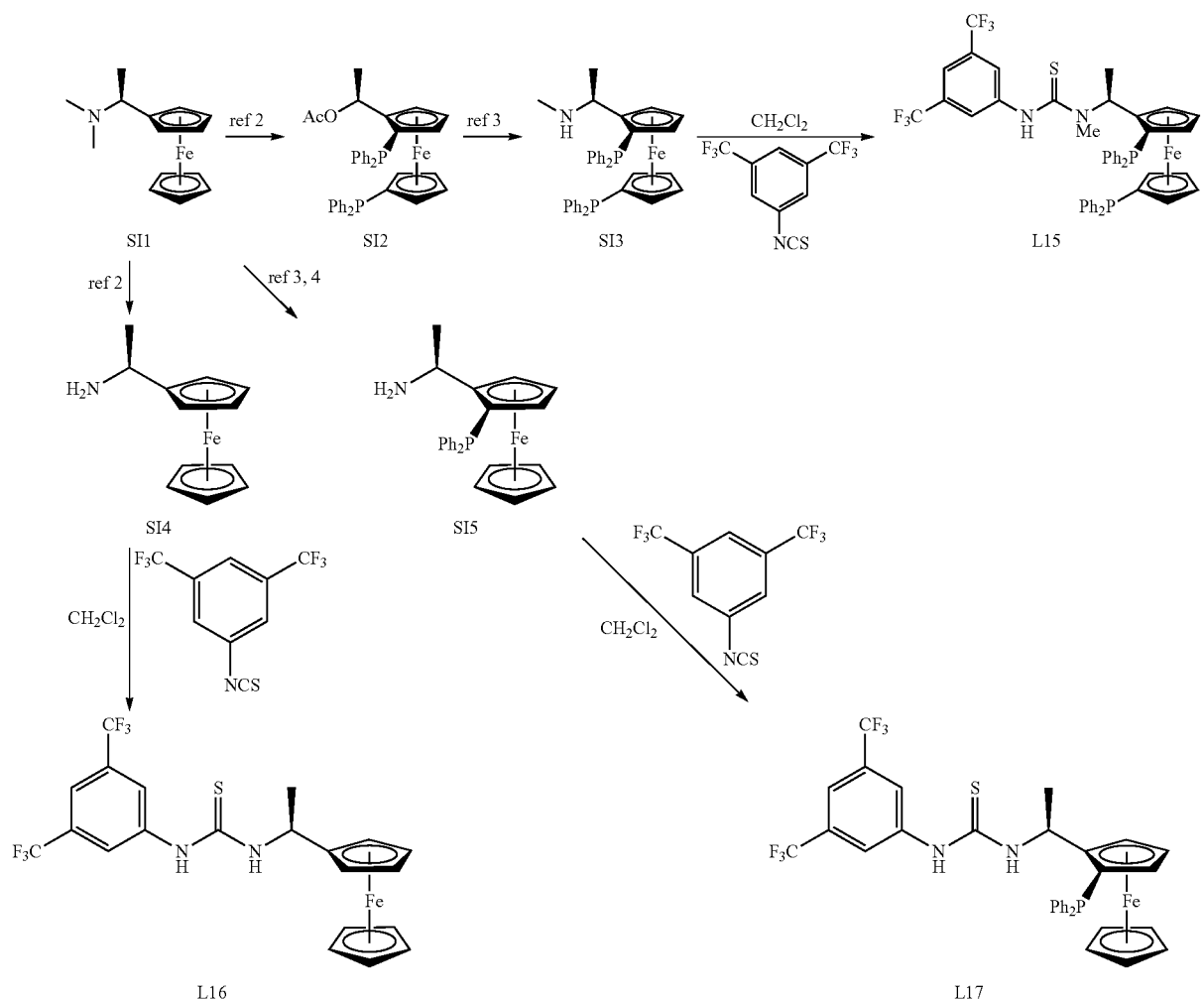

SI2 was prepared according the according the literature (Zhao, Q., et al., *Org. Lett.* 2013, 15, 4014-4017). SI3 was prepared according the according the literature (Gotov, B., et al., *New J. Chem.* 2000, 24, 597-602). Under a nitrogen atmosphere, 3,5-bis(trifluoromethyl)phenyl isothiocyanate (1.1 mmol) as added to a solution of SI3 (1.0 mmol) in dry DCM (1.0 ml). After the reaction mixture was stirred overnight, the reaction mixture was concentrated in vacuo. The residue was purified by flash column chromatography on silica gel (hexane/ethyl acetate=9/1 as eluant) gave L15 as yellow solid.

L15: $^1$H NMR (400 MHz, CDCl$_3$) δ 7.65 (s, 2H), 7.54 (s, 1H), 7.49-7.40 (m, 3H), 7.35-7.07 (m, 18H), 6.44 (s, 1H), 4.53 (d, J=6.0 Hz, 2H), 4.21 (d, J=15.6 Hz, 3H), 3.71 (s, 2H), 2.50 (s, 3H), 1.50 (d, J=6.7 Hz, 3H).

$^{13}$C NMR (100 MHz, CDCl$_3$) δ 180.28 (s), 141.45 (s), 138.82 (d, J=9.8 Hz), 138.30 (d, J=9.8 Hz), 135.78 (d, J=7.7 Hz), 134.88 (d, J=21.3 Hz), 133.42 (dd, J=33.4, 19.7 Hz), 132.53 (d, J=19.5 Hz), 131.28 (q, J=33.4 Hz), 129.43 (s), 129.01-128.44 (m), 128.28 (d, J=6.8 Hz), 128.16 (s), 124.61 (s), 123.89 (s), 121.90 (s), 117.57 (s), 93.41 (d, J=26.4 Hz), 75.47 (d, J=18.1 Hz), 74.42 (s), 73.56 (d, J=5.1 Hz), 73.40 (d, J=4.6 Hz), 72.18 (s), 71.75 (s), 54.83 (d, J=7.7 Hz), 31.93 (s), 15.64 (s).

$^{31}$P NMR (162 MHz, CDCl$_3$) δ -18.09 (s), -26.79 (s).

HRMS (ESI): [M+H$^+$] Calc. 883.1485. found 883.1583.

SI4 was prepared according the according the literature (Zhao, Q., et al., *Org. Lett.* 2013, 15, 4014-4017). Under an nitrogen atmosphere, 3,5-bis(trifluoromethyl)phenyl isothiocyanate (1.1 mmol) was added to a solution of SI4 (1.0 mmol) in dry DCM (1.0 ml). After the reaction mixture was stirred overnight, the reaction mixture was concentrated in vacuo. The residue was purified by flash column chromatography on silica gel (hexane/ethyl acetate=9/1 as eluant) gave L16 as yellow solid.

L16: $^1$H NMR (400 MHz, CDCl$_3$) δ 8.07 (s, 1H), 7.75 (d, J=10.5 Hz, 3H), 6.29 (s, 1H), 5.30 (s, 1H), 4.26-4.15 (m, 3H), 4.08 (s, 2H), 4.03 (s, 4H), 1.60 (d, J=6.5 Hz, 3H).

$^{13}$C NMR (100 MHz, CDCl$_3$) δ 179.16 (s), 138.72 (s), 133.43 (d, J=33.7 Hz), 124.42 (s), 124.07 (s), 121.36 (s), 119.84 (s), 90.06 (s), 68.59 (d, J=3.6 Hz), 68.27 (s), 67.41 (s), 65.57 (s), 50.14 (s), 19.99 (s). HRMS (ESI): [M$^+$] Calc. 500.0444. found 500.0452.

SI5 was prepared according the according the literature (Zhao, Q., et al., *Org. Lett.* 2013, 15, 4014-4017 and Hayashi, T., et al., *Bull. Chem. Soc. Jpn*, 1980, 53, 1138-1151). Under a nitrogen atmosphere, 3,5-bis(trifluoromethyl)phenyl isothiocyanate (1.1 mmol) was added to a solution of SI5 (1.0 mmol) in dry DCM (1.0 ml). After the reaction mixture was stirred overnight, the reaction mixture was concentrated in vacuo. The residue was purified by flash column chromatography on silica gel (hexane/ethyl acetate=9/1 as eluant) gave L17 as yellow solid.

L17: $^1$H NMR (400 MHz, CDCl$_3$) δ 7.74 (s, 3H), 7.51 (s, 2H), 7.40-7.28 (m, 5M), 7.22 (s, 3H), 7.15-7.05 (m, 2H), 5.59 (s, 1H) 4.51 (s, 1H), 4.32 (s, 1H), 3.96 (s, 5H), 3.79 (s, 1H), 1.46 (d, J=4.7 Hz, 3H).

$^{13}$C NMR (100 MHz, CDCl$_3$) δ 177.42 (s), 138.02 (s), 137.86 (d, J=6.0 Hz), 134.85 (d, J=4.5 Hz), 133.73 (d, J=20.8 Hz), 131.89 (d, J=33.9 Hz), 131.25 (d, J=17.8 Hz), 128.51 (s), 127.43-127.02 (m), 126.10-125.89 (m), 123.82 (s), 123.27 (s), 120.56 (s), 118.42 (s), 118.01-117.76 (m), 93.98 (d, J=24.2 Hz), 72.16 (s), 71.07 (d, J=4.0 Hz), 70.22 (s), 68.83 (s), 68.66 (s), 50.33 (s), 21.26 (s).

$^{31}$P NMR (162 MHz, CDCl$_3$) δ −24.67 (s).

HRMS (ESI): [M+H$^+$] Calc. 685.0964. found 685.0950.

Example 2—Asymmetric Hydrogenation of Nitroalkenes

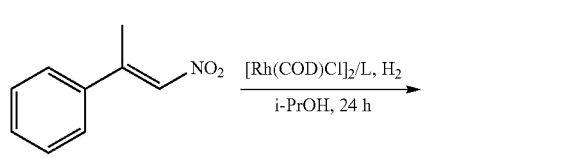

to remove the metal complex. The product (2a) was analyzed by NMR spectroscopy for conversion and chiral HPLC for ee values.

(R)-2a: $^1$H NMR (400 MHz, CDCl$_3$) δδ 7.38-7.31 (m, 2H), 7.30-7.20 (m, 3H), 4.58-4.46 (m, 1H), 3.85-3.16 (m, 1H), 1.38 (d, J=7.0 Hz, 1H). $^{13}$C NMR (100 MHz, CDCl$_3$) δ 140.93 (s), 128.98 (s), 127.57 (s), 126.90 (s), 81.87 (s), 38.65 (s), 18.73 (s). HPLC: OD, 215 nm, hexane/2-propanol=98:2, flow rate 0.9 mL/min, $t_R$ (major)=19.4 min, $t_R$ (minor)=27.4 min. $[α]_D^{25}$=+41.4° (c=0.67, CHCl$_3$).

TABLE 1

Study of effects of pressure, concentration, and temperature.[a]

| Entry | Solvent | Rh-L8 | H$_2$ [atm] | S/C | V (mL) | T [° C.] | 2a [%][b] | ee [%][c] |
|---|---|---|---|---|---|---|---|---|
| 1 | i-PrOH | [Rh(COD)Cl]$_2$ | 5 | 50 | 0.25 | 25 | >99 | 99 |
| 2 | i-PrOH | [Rh(COD)Cl]$_2$ | 5 | 100 | 0.25 | 35 | >99 | 99 |
| 3 | i-PrOH | [Rh(COD)Cl]$_2$ | 5 | 200 | 0.25 | 35 | 97 | 98 |
| 4 | i-PrOH | [Rh(COD)Cl]$_2$ | 5 | 400 | 0.25 | 35 | 90 | 98 |
| 5 | i-PrOH | [Rh(COD)Cl]$_2$ | 10 | 200 | 0.25 | 35 | 97 | 99 |
| 6 | i-PrOH | [Rh(COD)Cl]$_2$ | 20 | 200 | 0.25 | 35 | >99 | 98 |
| 7 | i-PrOH | [Rh(COD)Cl]$_2$ | 20 | 400 | 0.25 | 35 | 95 | 98 |
| 8 | i-PrOH | [Rh(COD)Cl]$_2$ | 30 | 400 | 0.25 | 35 | 98 | 98 |
| 9 | i-PrOH | [Rh(COD)Cl]$_2$ | 5 | 100 | 0.5 | 35 | 99 | 98 |
| 10 | i-PrOH | [Rh(COD)Cl]$_2$ | 5 | 100 | 1.0 | 35 | 97 | 98 |
| 11 | i-PrOH | [Rh(COD)Cl]$_2$ | 5 | 400 | 0.25 | 45 | 90 | 94 |

[a]Unless orthwerwise mentioned, reactions were performed with 1a (0.1 mmol) and a 1a/Rh/L ratio of 1/1.1/1.1.
[b]Conversions were determined by $^1$H NMR spectroscopy of the crude reaction mixture and HPLC analysis.
[c]Determined by HPLC analysis on a chiral stationary phase.

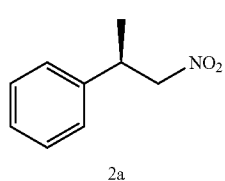

In a nitrogen-filled glovebox, a solution of L (2.2 eqv.) and [Rh(COD)Cl]$_2$ (3.0 mg, 0.006 mmol) in 3.0 mL anhydrous i-PrOH was stirred at room temperature for 30 min. A specified amount of the resulting solution (0.25 mL) was transferred to a vial charged with 1a (0.1 mmol) by syringe. The vials were transferred to an autoclave, which was then charged with 5 atm of H$_2$ and stirred at 35° C. for 24 h. The hydrogen gas was released slowly and the solution was concentrated and passed through a short column of silica gel β,β-disubstituted nitroalkanes were prepared using the general procedure set forth above with different nitroalkenes. Nitroalkenes with various substituents at the phenyl ring were tolerated. Meta and para substitutions led to excellent results whether they were electron-withdrawing or electron-donating groups. The ortho-methoxy group resulted in a lower conversion and enantioselectivity. This catalytic system also provided enantiomerically β-ethyl nitroalkane with good conversion and excellent enantioselectivity. The nitroalkanes were characterized as follows:

(R)-2b: $^1$H NMR (400 MHz, CDCl$_3$) δ 7.39-6.86 (m, 5H), 4.47-4.36 (m, 2H), 3.47-3.49 (m, 1H), 2.25 (s, 3H), 1.28 (d, J=7.0 Hz, 3H). $^{13}$C NMR (100 MHz, CDCl$_3$) δ 137.87 (s), 137.21 (s), 129.61 (s), 126.73 (s), 81.98 (s), 38.27 (s), 20.98 (s), 18.75 (s). HPLC: OD, 215 nm, hexane/2-propanol=98:2, flow rate 0.9 mL/min, $t_R$ (major)=14.1 min, $t_R$ (minor)=23.0 min. $[α]_D^{25}$=+42.9° (c=0.51, CHCl$_3$)

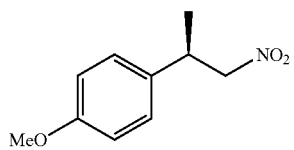

(R)-2c: $^1$H NMR (400 MHz, CDCl$_3$) δ 7.19-7.11 (m, 2H), 6.96-6.84 (m, 2H), 4.52-4.42 (m, 2H), 3.79 (s, 3H), 3.66-

3.54 (m, 1H), 1.35 (d, J=7.0 Hz, 3H). $^{13}$C NMR (100 MHz, CDCl$_3$) δ 158.94 (s), 132.86 (s), 127.89 (s), 114.34 (s), 82.12 (s), 55.26 (s), 37.92 (s), 18.79 (s). HPLC: OD, 215 nm, hexane/2-propanol=98:2, flow rate 0.9 mL/min, t$_R$ (major)=22.1 min, t$_R$ (minor)=40.6 min. $[\alpha]_D^{25}$=+35.8° (c=0.51, CHCl$_3$)

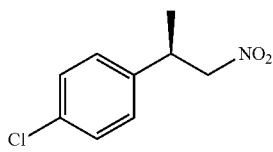

(R)-2d: $^1$H NMR (400 MHz, CDCl$_3$) δ 7.37-7.27 (m, 2H), 7.21-7.12 (m, 2H), 4.63-4.42 (m, 2H), 3.75-3.48 (m, 1H), 1.37 (d, J=7.0 Hz, 3H). $^{13}$C NMR (100 MHz, CDCl$_3$) δ 139.35 (s), 133.43 (s), 129.15 (s), 128.27 (s), 81.56 (s), 38.07 (s), 18.71 (s). HPLC: OD, 215 nm, hexane/2-propanol=98:2, flow rate 0.9 mL/min, t$_R$ (major)=18.8 mm, t$_R$ (minor)=27.1 min. $[\alpha]_D^{25}$=+39.5° (c=0.48, CHCl$_3$)

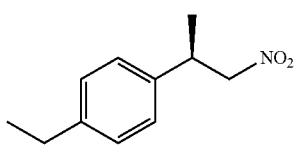

(R)-2e: $^1$H NMR (400 MHz, CDCl$_3$) δ 7.18-7.13 (m, 4H), 4.56-4.43 (m, 2H), 3.70-3.48 (m, 1H), 2.63 (q, J=7.6 Hz, 2H), 1.36 (d, J=7.0 Hz, 3H), 1.22 (t, J=7.6 Hz, 3H). $^{13}$C NMR (100 MHz, CDCl$_3$) δ 143.58 (s), 138.10 (s), 128.43 (s), 126.83 (s), 82.01 (s), 38.30 (s), 28.42 (s), 18.75 (s), 15.42 (s). HPLC: OD, 215 nm, hexane/2-propanol=98:2, flow rate 0.9 mL/min, t$_R$ (major)=11.8 min, t$_R$ (minor)=19.9 min. $[\alpha]_D^{25}$=+54.3° (c=0.44, CHCl$_3$).

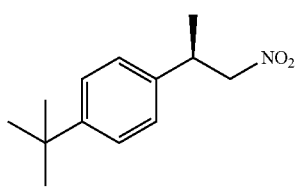 [SMILES: C[C@@H](C[N+](=O)[O-])c1ccc(C(C)(C)C)cc1]

(R)-2f: $^1$H NMR (400 MHz, CDCl$_3$) δ 7.37-7.32 (m, 2H), 7.18-7.12 (m, 2H), 4.56-4.43 (m, 2H), 3.69-3.51 (m, 1H), 1.37 (d, J=7.0 Hz, 3H), 1.30 (s, 3H). $^{13}$C NMR (100 MHz, CDCl$_3$) δ 150.47 (s), 137.79 (s), 126.55 (s), 125.84 (s), 81.97 (s), 38.13 (s), 34.47 (s), 31.29 (s), 18.67 (s). HPLC: OD, 215 nm, hexane/2-propanol=98:2, flow rate 0.9 mL/min, t$_R$ (major)=9.7 min, t$_R$ (minor)=18.4 min. $[\alpha]_D^{25}$=+41.8° (c=1.0, CHCl$_3$)

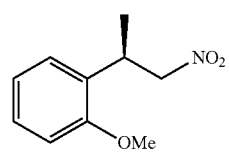

(R)-2g: $^1$H NMR (400 MHz, CDCl$_3$) δ 7.30-7.22 (m, 1H), 7.16 (dd, J=7.6, 1.6 Hz, 1H), 6.96-6.88 (m, 2H), 4.68 (dd, J=11.9, 6.0 Hz, 1H), 4.46 (dd, J=11.9, 8.8 Hz, 1H), 3.97-3.90 (m, 1H), 3.88 (s, 3H), 1.38 (d, J=7.0 Hz, 3H). $^{13}$C NMR (100 MHz, CDCl$_3$) δ 157.06 (s), 128.82 (s), 128.51 (s), 127.71 (s), 120.86 (s), 110.83 (s), 80.45 (s), 55.34 (s), 33.48 (s), 17.05 (s). HPLC: OD, 21.5 nm, hexane/2-propanol=98:2, flow rate 0.9 mL/min, t$_R$ (major)=14.4 min, t$_R$ (minor)=17.0 min. $[\alpha]_D^{25}$=+6.9 (c=0.2, CHCl$_3$).

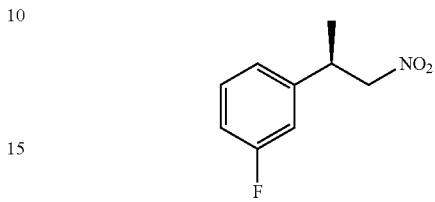

(R)-2h: $^1$H NMR (400 MHz, CDCl$_3$) δ 7.35-7.27 (m, 1H), 7.05-6.87 (m, 1H), 4.57-4.45 (m, 2H), 3.69-3.62 (m, 1H), 1.38 (d, J=7.0 Hz, 3H). $^{13}$C NMR (100 MHz, CDCl$_3$) δ 164.33 (s), 161.88 (s), 143.46 (d, J=7.0 Hz), 130.57 (d, J=8.3 Hz), 122.65 (d, J=2.9 Hz), 114.59 (d, J=21.0 Hz), 113.96 (d, J=21.8 Hz), 81.51 (s), 38.37 (d, J=1.6 Hz), 18.67 (s). HPLC: OD, 215 nm, hexane/2-propanol=98:2, flow rate 0.9 mL/min, t$_R$ (major)=20.0 min, t$_R$ (minor)=28.4 min. $[\alpha]_D^{25}$=+33.3° (c=0.72, CHCl$_3$).

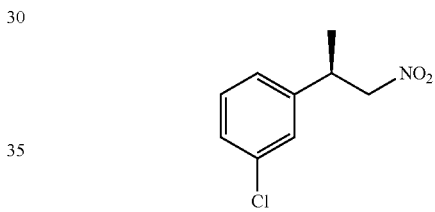

(R)-2i: $^1$H NMR (400 MHz, CDCl$_3$) δ 7.31-7.21 (m, 3H), 7.12-7.10 (m, 1H), 4.56-4.45 (m, 2H), 3.70-3.55 (m, 1H), 1.37 (d, J=7.0 Hz, 3H). $^{13}$C NMR (100 MHz, CDCl$_3$) δ 142.94 (s), 134.83 (s), 130.26 (s), 127.84 (s), 127.17 (s), 125.18 (s), 81.41 (s), 38.33 (s), 18.65 (s). HPLC: OD, 215 nm, hexane/2-propanol=98:2, flow rate 0.9 mL/min, t$_R$ (major)=19.8 min, t$_R$ (minor)=30.5 min. $[\alpha]_D^{25}$=+37.1° (c=0.58, CHCl$_3$)

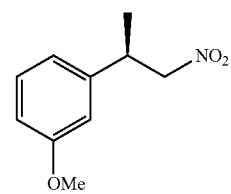

(R)-2j: $^1$H NMR (400 MHz, CDCl$_3$) δ 7.26 (t, J=7.9 Hz, 1H), 6.96-6.68 (m, 3H), 4.57-4.44 (m, 2H), 3.80 (s, 3H), 3.66-3.54 (m, 1H), 1.37 (d, J=7.0 Hz, 3H). $^{13}$C NMR (100 MHz, CDCl$_3$) δ 160.00 (s), 142.54 (s), 130.01 (s), 119.11 (s), 113.10 (s), 112.55 (s), 81.79 (s), 77.34 (s), 77.03 (s), 76.71 (s), 55.23 (s), 38.66 (s), 18.70 (s). HPLC: OD, 215 nm, hexane/2-propanol=95:5, flow rate 0.9 mL/min, t$_R$ (major)=29.3 min, t$_R$ (minor)=52.2 min. $[\alpha]_D^{25}$=+40.6° (c=0.73, CHCl$_3$)

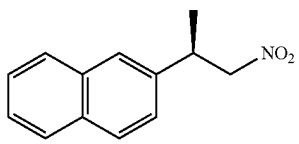 [SMILES: C[C@@H](C[N+](=O)[O-])c1ccc2ccccc2c1]

(R)-2k: ¹H NMR (400 MHz, CDCl₃) δ 8.08-7.70 (m, 3H), 7.67 (d, J=1.0 Hz, 1H), 7.56-7.40 (m, 2H), 7.35 (dd, J=8.5, 1.8 Hz, 1H), 4.67-4.54 (m, 2H), 4.02-3.55 (m, 1H), 1.47 (d, J=7.0 Hz, 2H). ¹³C NMR (100 MHz, CDCl₃) δ 138.29, 133.52, 132.78, 128.85, 127.76, 127.69, 126.44, 126.08, 125.78, 124.81, 81.80, 38.80, 18.79. HPLC: OD, 215 nm, hexane/2-propanol=80:20, flow rate 0.9 mL/min, $t_R$ (major)=19.8 min, $t_R$ (minor)=53.5 min. $[\alpha]_D^{25}$=+36.8° (c=0.9, CHCl₃)

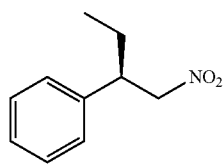

(R)-2l: ¹H NMR (400 MHz, CDCl₃) δ 7.39-7.23 (m, 3H), 7.21-7.10 (m, 2H), 4.59-4.51 (m, 2H), 3.54-3.11 (m, 1H), 1.79-1.66 (m, 2H), 0.84 (t, J=7.4 Hz, 3H). ¹³C NMR (100 MHz, CDCl₃) δ 139.33, 128.89, 127.56, 80.76, 46.00, 26.18, 11.49. HPLC: OD, 215 nm, hexane/2-propanol=98:2, flow rate 0.9 mL/min, $t_R$ (major)=16.0 min, $t_R$ (minor)=27.7 min. $[\alpha]_D^{25}$=+35.5° (c=0.54, CHCl₃)

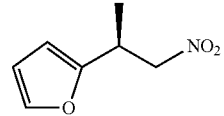

(S)-2m: ¹H NMR (400 MHz, CDCl₃) δ 6.26-6.23 (m, 1H), 6.05 (d, J=3.1 Hz, 1H), 4.59 (dd, J=12.2, 6.6 Hz, 1H), 4.36 (dd, J=12.2, 8.0 Hz, 1H), 3.72-3.60 (m, 1H), 1.31 (d, J=7.0 Hz, 3H). ¹³C NMR (100 MHz, CDCl₃) δ 152.85 (s), 141.08 (s), 109.27 (s), 104.92 (s), 78.49 (s), 31.41 (s), 15.12 (s). HPLC: OD, 215 nm, hexane/2-propanol=99.5:0.5, flow rate 0.9 mL/min, $t_R$ (major)=27.5 min, $t_R$ (minor)=30.7 min.

Example 3—Asymmetric Hydrogenation of N—H Imines

All N—H imines were prepared according the literature (Hou, G., et al., *J. Am. Chem. Soc.* 2009, 131, 9882-9883.). All the spectral data are consistent with the literature values.

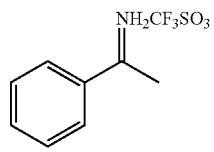

¹H NMR (400 MHz, CDCl₃) δ 11.46 (s, 2H), 8.20-7.91 (m, 2H), 7.78 (t, J=7.5 Hz, 1H), 7.61 (dd, J=17.7, 9.6 Hz, 2H), 2.94 (d, J=5.2 Hz, 3H).
¹³C NMR (100 MHz, CDCl₃) δ 186.36 (s), 136.95 (s), 129.92 (s), 129.35 (s), 129.33 (s), 21.73 (s).

General Procedure:

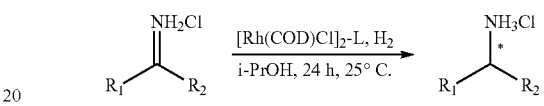

In a nitrogen-filled glovebox a solution of L14 (2.2 eqv.) and [Rh(COD)Cl]₂ (3.0 mg, 0.006 mmol) in 6.0 mL anhydrous i-PrOH was stirred at room temperature for 30 min.

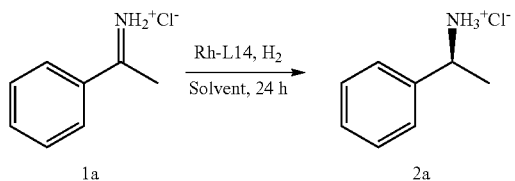

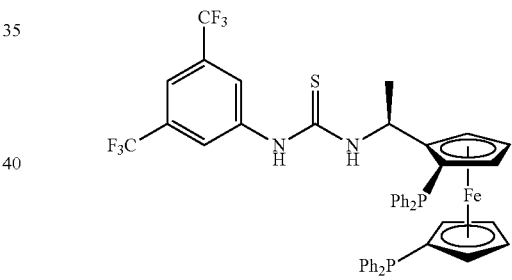

A specified amount of the resulting solution (1 mL) was transferred to a vial charged with 1a (0.1 mmol) by syringe. The vials were transferred to an autoclave, which was then charged with 10 atm of H₂ and stirred at 25° C. for 24 h. The resulting mixture was concentrated under vacuum and dissolved in saturated aqueous NaHCO₃ (5 mL). After stirring for 10 min, the mixture was extracted with CH₂Cl₂ (3×2 mL) and dried over Na₂SO₄. To the resulting solution was added Ac₂O (300 μL) and stirred for 30 min. The resulting solution was then analyzed for conversion and ee directly by GC. The product was purified by chromatography on silica gel column with dichloromethane/methanol (90:10). All spectral data were consistent with the literature values (Hou. G., et al., *J. Am. Chem. Soc.* 2009, 131, 9882-9883).

TABLE 2

Study of metal salts.

| Entry | Solvent | Metal | H₂ [atm] | S/C | V [mL] | T [° C.] | Conv. [%][b] | ee [%][c] |
|---|---|---|---|---|---|---|---|---|
| 1 | i-PrOH | [Rh(COD)Cl]₂ | 20 | 25 | 1 | 35 | 99 | 92 |
| 2 | i-PrOH | [Ir(COD)Cl]₂ | 20 | 25 | 1 | 35 | 90 | 84 |

TABLE 2-continued

Study of metal salts.

| Entry | Solvent | Metal | $H_2$ [atm] | S/C | V [mL] | T [°C.] | Conv. [%][b] | ee [%][c] |
|---|---|---|---|---|---|---|---|---|
| 3 | i-PrOH | Rh(COD)$_2$BF$_4$ | 20 | 25 | 1 | 35 | 93 | 77 |
| 4 | i-PrOH | Rh(NBD)$_2$SbF$_6$ | 20 | 25 | 1 | 35 | 95 | 17 |
| 5 | i-PrOH | Pd(OAc)$_2$ | 20 | 25 | 1 | 35 | <1 | ND |
| 6 | i-PrOH | Pd(TFA)$_2$ | 20 | 25 | 1 | 35 | 30 | 0 |
| 7 | i-PrOH | [{RuCl$_2$(p-cymene)}$_2$] | 20 | 25 | 1 | 35 | 8 | 23 |

[a] Unless ortherwise mentioned, reactions were performed with 1a (0.1 mmol) and a Metal/L14 ratio of 1/1.1.
[b] Determined by GC analysis of the corresponding acetamides.
ND = not determined.

TABLE 3

Study of pressure and temperature.

| Entry | Solvent | $H_2$ [atm] | S/C | V (mL) | T [°C.] | Conv. [%][b] | ee [%][c] |
|---|---|---|---|---|---|---|---|
| 1 | i-PrOH | 20 | 25 | 1 | 35 | 99 | 92 |
| 2 | i-PrOH | 20 | 50 | 1 | 35 | 99 | 93 |
| 3 | i-PrOH | 20 | 100 | 1 | 35 | 99 | 93 |
| 4 | i-PrOH | 10 | 100 | 1 | 25 | 99 | 94 |
| 5 | i-PrOH | 10 | 200 | 1 | 25 | 96 | 94 |
| 6 | i-PrOH | 10 | 400 | 1 | 25 | 86 | 93 |
| 7 | i-PrOH | 20 | 200 | 1 | 25 | 97 | 93 |
| 8 | i-PrOH | 20 | 200 | 1 | 35 | 97 | 92 |
| 9 | i-PrOH | 20 | 400 | 1 | 35 | 90 | 93 |

[a] Reactions were performed with 1a (0.1 mmol) and a [Rh(COD)Cl]$_2$/L14 ratio of 1/1.1.
[b] Determined by GC analysis of the corresponding acetamides.

TABLE 4

Study of additives.

| Entry | Solvent | $H_2$ [atm] | S/C | Additive | T [°C.] | Conv. [%][b] | ee [%][b] |
|---|---|---|---|---|---|---|---|
| 1 | i-PrOH | 20 | 50 | 4A MS (100 mg) | 35 | 67 | 53 |
| 2 | i-PrOH | 20 | 50 | CF$_3$COOH (10 mmol %) | 35 | 99 | 75 |
| 3 | i-PrOH | 20 | 50 | CH$_3$COOH (10 mmol %) | 35 | 98 | 79 |
| 4 | i-PrOH | 20 | 50 | Et$_3$N (10 mmol %) | 35 | 63 | 35 |

[a] Reactions were performed with 1a (0.1 mmol) and a [Rh(COD)Cl]$_2$/L14 ratio of 1/2.2.
[b] Determined by GC analysis of the corresponding acetamides.

TABLE 5

Solvent study.

| Entry | Solvent | Metal source | Covn.[b](%) | ee[b](%) |
|---|---|---|---|---|
| 1 | i-PrOH | [Rh(COD)$_2$]BF$_4$ | 93 | 77 |
| 2 | i-PrOH | [Rh(NBD)$_2$]SbF$_6$ | 95 | 47 |
| 3 | i-PrOH | [Rh(COD)Cl]$_2$ | 99 | 92 |
| 4 | CH$_2$Cl$_2$ | [Rh(COD)Cl]$_2$ | 91 | 30 |
| 5 | Toluene | [Rh(COD)Cl]$_2$ | 60 | 15 |
| 6 | THF | [Rh(COD)Cl]$_2$ | 76 | 60 |
| 7 | MeOH | [Rh(COD)Cl]$_2$ | 99 | 73 |
| 8 | EtOH | [Rh(COD)Cl]$_2$ | 92 | 89 |
| 9 | t-BuOH | [Rh(COD)Cl]$_2$ | 84 | 91 |
| 10[c] | i-PrOH | [Rh(COD)Cl]$_2$ | 99 | 93 |
| 11[d] | i-PrOH | [Rh(COD)Cl]$_2$ | 99 | 94 |
| 12[e] | i-PrOH | [Rh(COD)Cl]$_2$ | 96 | 94 |
| 11[f] | i-PrOH | [Rh(COD)Cl]$_2$ | 97 | 93 |
| 14[g] | i-PrOH | [Rh(COD)Cl]$_2$ | 97 | 92 |

[a] Unless otherwise mentioned, reactions were performed with 1a (0.1 mmol) and a Rh/L/1a ratio of 1/1.1/25 in 1.0 mL solvent at 35° C. under 20 atm $H_2$.
[b] Determined by GC analysis of the corresponding acetamides.
[c] S/C = 100, 35° C., 20 atm $H_2$.
[d] S/C = 100, 25° C., 10 atm $H_2$.
[e] S/C = 100, 25° C., 10 atm $H_2$.
[f] S/C = 200, 25° C., 20 atm $H_2$.
[g] S/C = 200, 35° C., 20 atm $H_2$.
COD = 1,5-cyclooctadiene, NBD = 2,5-norbornadiene.

A variety of N—H imines were tested. Most substrates with meta and para substitutions on the phenyl ring afforded high yields and enantioselectivities (96-99% yield and 90-94% ee).

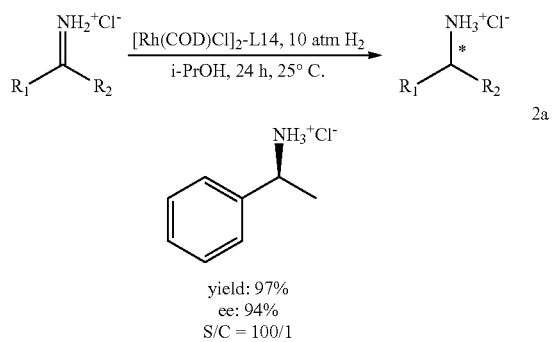

2a
yield: 97%
ee: 94%
S/C = 100/1

2b
yield: 94%
ee: 95%
S/C = 100/1

2c
yield: 97%
ee: 90%
S/C = 50/1

-continued

2d
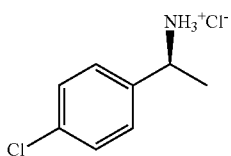
yield: 84%
ee: 90%
S/C = 50/1

2e
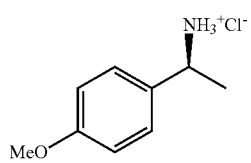
yield: 66%
ee: 93%
S/C = 50/1

2f
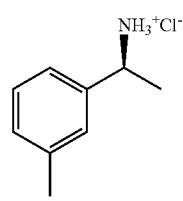
yield: 92%
ee: 93%
S/C = 50/1

2g
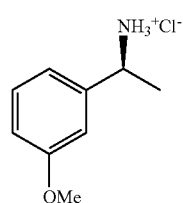
yield: 82%
ee: 94%
S/C = 50/1

2h
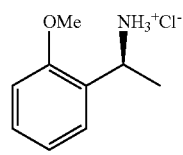
yield: 34%
ee: 84%
S/C = 50/1

2i
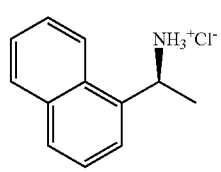
yield: 93%
ee: 95%
S/C = 50/1

-continued

2j
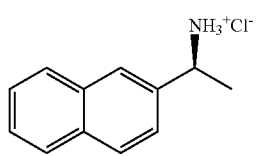
yield: 95%
ee: 92%
S/C = 50/1

2k
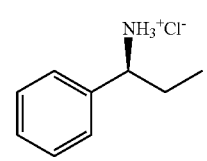
yield: 82%
ee: 87%
S/C = 50/1

2l
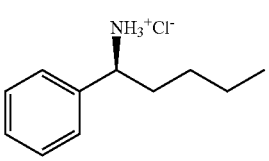
yield: 70%
ee: 75%
S/C = 50/1

However, the chloro group and methoxy group resulted in an obvious decrease of the yields (2d, 2e and 2g). The ortho-methoxy group on the phenyl ring resulted in 34% yield and 84% ee (2h). Products with 1- and 2-naphthyl group were obtained with 92% ee and 93% ee respectively. Changing the $R_2$ group had a significant effect on the outcome. When $R_2$ was ethyl, both lower conversion and enantioselectivity were observed (2k). As the $R_2$ group was changed to butyl, further loss of the conversion and enantioselectivity was observed (70% yield and 75% ee, 2l).

To obtain insight into this catalytic system, a series of chiral ligands were prepared and control experiments were undertaken.

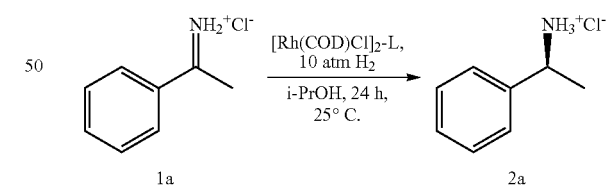

L9
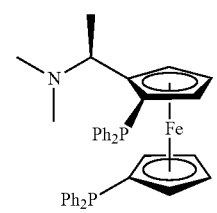

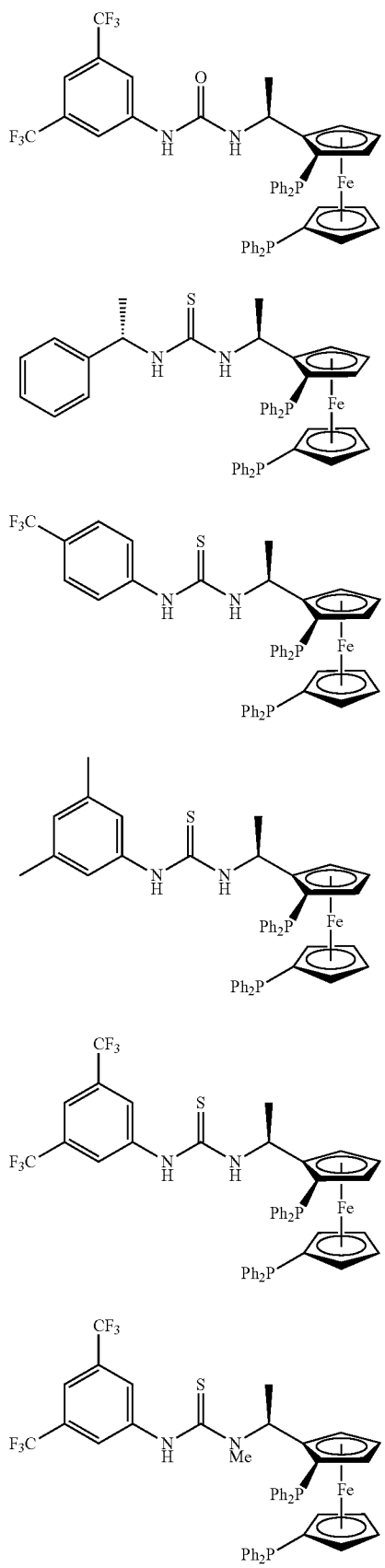

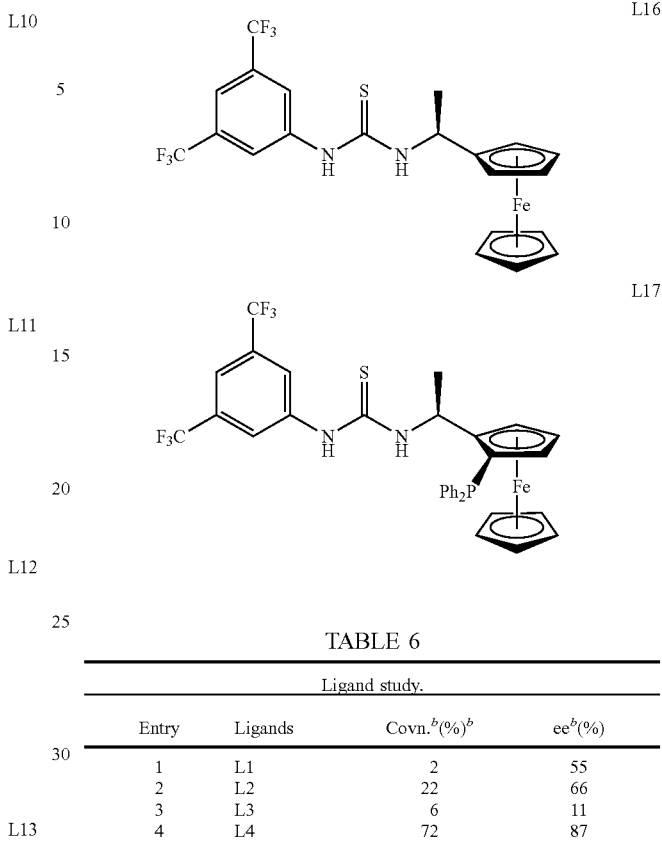

TABLE 6

Ligand study.

| Entry | Ligands | Covn.[b](%)[b] | ee[b](%) |
|---|---|---|---|
| 1 | L1 | 2 | 55 |
| 2 | L2 | 22 | 66 |
| 3 | L3 | 6 | 11 |
| 4 | L4 | 72 | 87 |
| 5 | L5 | 76 | 90 |
| 6 | L6 | 99 | 94 |
| 7 | L7 | 26 | 38 |
| 8 | L8 | 2 | 11 |
| 9 | L9 | 9 | 84 |
| 10[c] | L8 | 5 | 8 |
| 11[d] | L1 | 9 | 57 |

[a] Unless otherwise mentioned, reactions were performed with 1a (0.1 mmol) and a Rh/L/1a ratio of 1/1.1/100 in 1.0 mL solvent at 25° C. under 10 atm H₂.
[b] Determined by GC analysis of the corresponding acetamides.
[c] Rh/L/1a/Ph₃P = 1/1.1/100/2.2.
[d] Rh/L/1a/thiourea = 1/1.1/100/1.1.

The Rh-bisphosphine complex without a (thio)urea (L9) showed very low activity and enantioselectivity (Table 6, entry 1). Urea L10 provided 22% conversion and 66% ee in sharp contrast with the more acidic thiourea L14 (Table 6, entry 2 vs. 6).[1a] The CF₃ group on the 3,5-(trifluoromethyl) phenyl moiety remained important in the catalytic system (Table 6, entries 3-5). Further, several modified ligands were prepared and screened. An N-methylation of L14 led to a dramatic decrease of the conversion and enantioselectivity (Table 6, entry 7). This finding suggested that the NH was involved in the activation of iminium salts and the stereoselectivity of hydrogenation. Furthermore, the low conversion and enantioselectivity obtained with monodentate phosphorus ligands implied that a bisphosphine moiety was essential (Table 6, entry 9). Importantly, neither the combination of the chiral phosphine with the 3,5-bistrifluoromethylphenyl thiourea, nor the combination of the chiral thiourea with the simple phosphine improved this reaction (Table 6, entry 1 vs. 11, entry 8 vs. 10), which pointed to the importance of the covalent linker for high activity and enantioselectivity.

Different counterions and additives were also investigated. When the chloride counterion in 1a was replaced with trifluoromethanesulfonate, only 20% conversion and 53% ee was observed (Table 7, entry 1). The addition of a chloride counterion increased the conversions and enantioselectivities (entries 2 and 3). However, the addition of bromide and iodide counterions decreased the conversions and enantioselectivities (entries 4-6).

TABLE 3

Substrates study and control experiments.[a]

| Entry | 1  | Additive | Conv.[b](%) | ee[b](%) |
|-------|----|----------|-------------|----------|
| 1     | 1m | —        | 20          | 53       |
| 2     | 1m | TBAC     | 86          | 94       |
| 3     | 1m | LiCl     | 71          | 93       |
| 4     | 1a | —        | 99          | 94       |
| 5     | 1a | TBAB     | 77          | 90       |
| 6     | 1a | TBAI     | 32          | 89       |

[a]Unless otherwise mentioned, reactions were performed with 1a (0.1 mmol) and a Rh/L/1a/Additive ratio of 1/1.1/100/100 in 1.0 mL solvent.
[b]Determined by GC analysis of the corresponding acetamides.
[c]Determined by $^1$H NMR.
TBAC = tetrabutylammonium chloride,
TBAB = tetrabutylammonium bromide,
TBAI = tetrabutylammonium iodide.
ND = not detertimined.

Further information about the reaction was obtained by $^1$H NMR studies of mixtures generated from ligands and TBAC. The addition of varying amounts of TBAC to L14 in CDCl$_3$ resulted in downfield shifts of the NH proton signals. At 1.0 equivalents of TBAC, the signal for NH was at 9.73 ppm, but when 3.0 equivalents of TBAC were added, the NH signal appeared at 10.16 ppm. Analogous experiments employing a series of different ligands and TBAC gave similar results. This finding was consistent with a hydrogen-bonding interaction between the catalyst's thiourea and chloride ions. This observation, coupled with the fact that optimal yields and ee values involve chloride ions, led us to propose that catalytic chloride-bound intermediates are involved in the mechanism.

The present invention has been described with particular reference to the preferred embodiments. It should be understood that the foregoing descriptions and examples are only illustrative of the invention. Various alternatives and modifications thereof can be devised by those skilled in the art without departing from the spirit and scope of the present invention. Accordingly, the present invention is intended to embrace all such alternatives, modifications, and variations that fall with the scope of the appended claims.

What is claimed is:

1. A ligand selected from the group consisting of compounds represented by the following formulae:

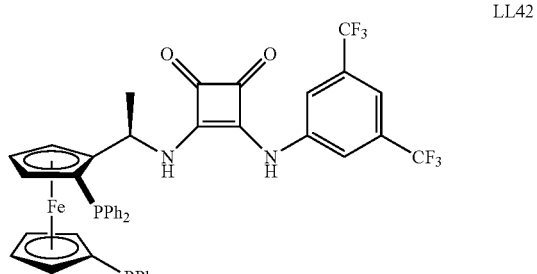

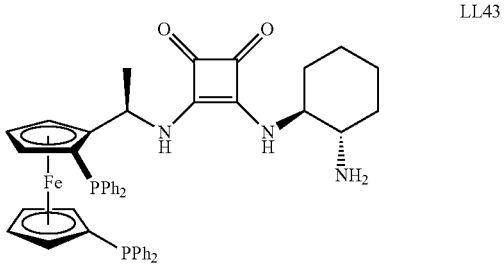

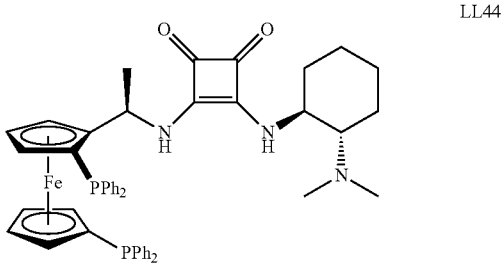

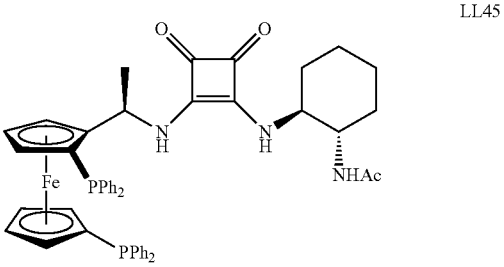

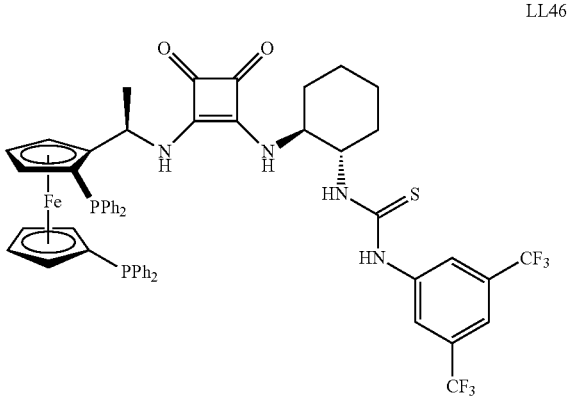

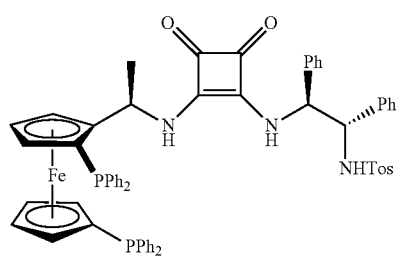
LL47
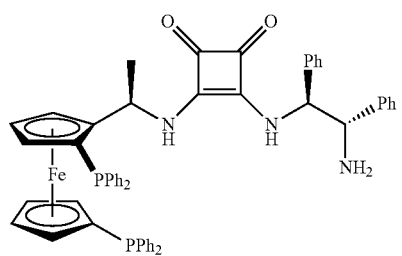
LL48
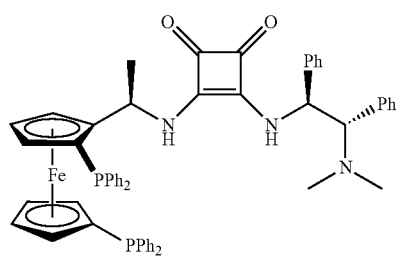
LL49
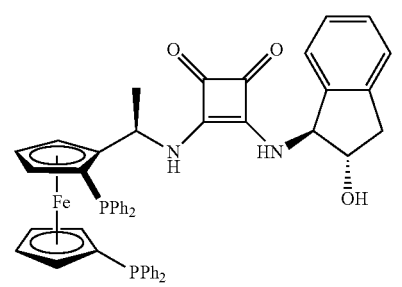
LL50
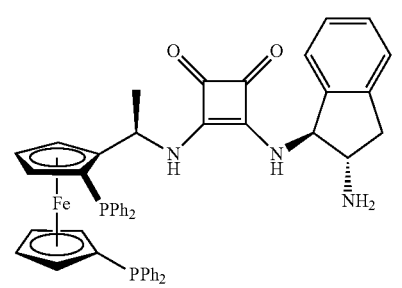
LL51
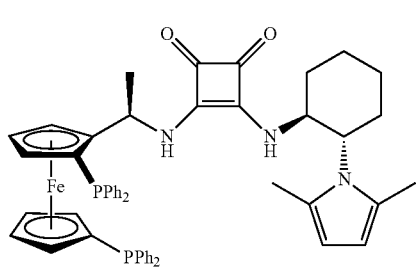
LL52
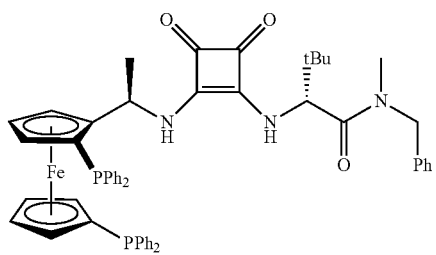
LL53
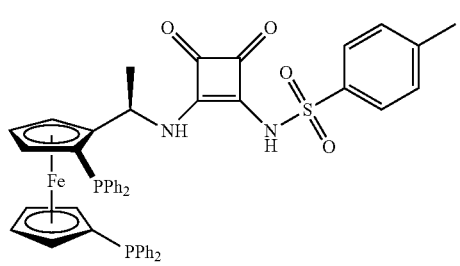
LL54
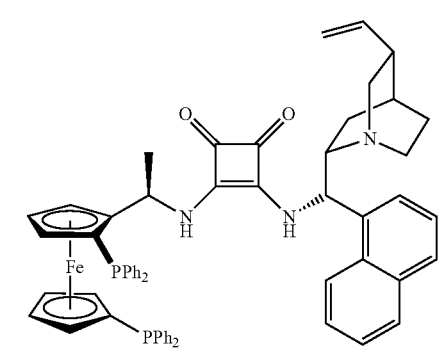
LL55
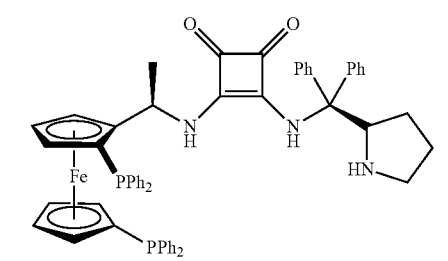
LL56
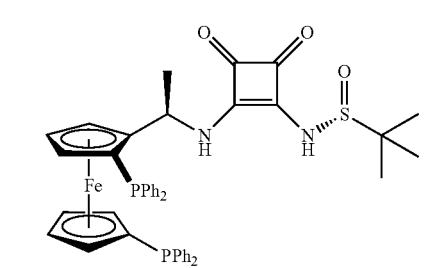
LL57

LL1
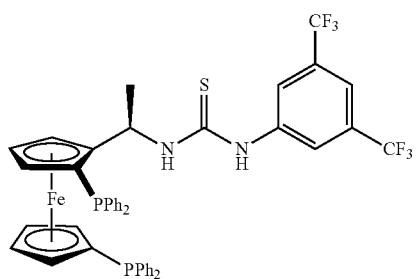
LL2
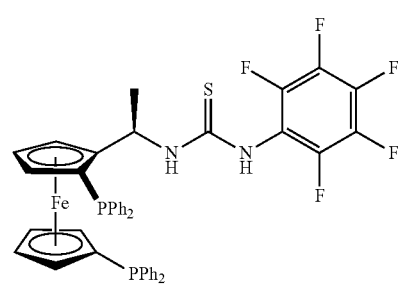
LL3
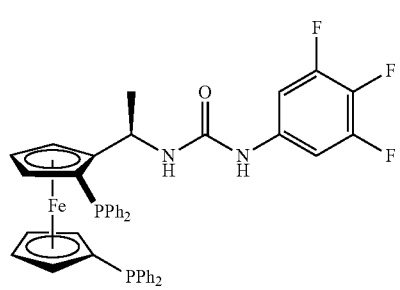
LL4
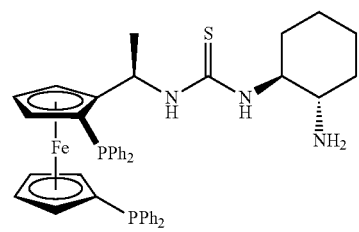
LL5
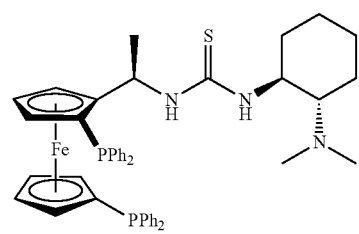
LL6
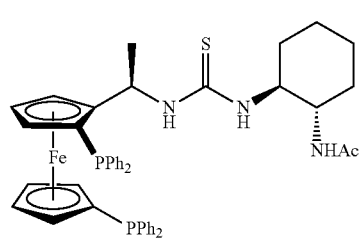
LL7
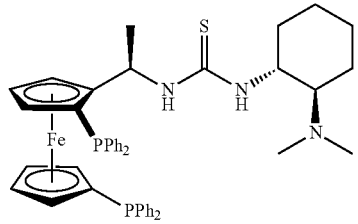
LL8
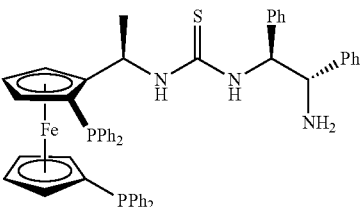
LL9
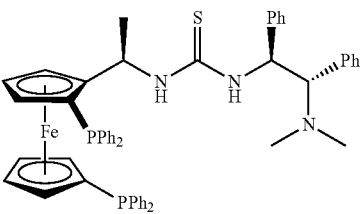
LL10
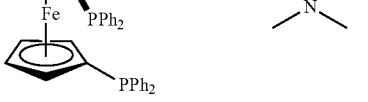
LL11
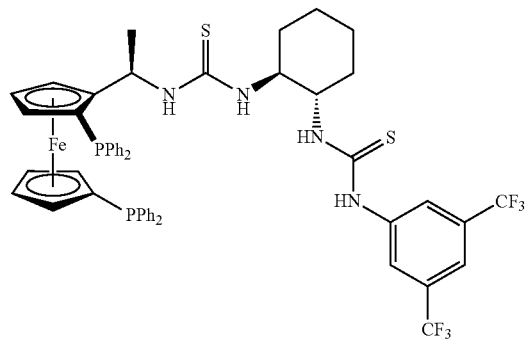
LL12
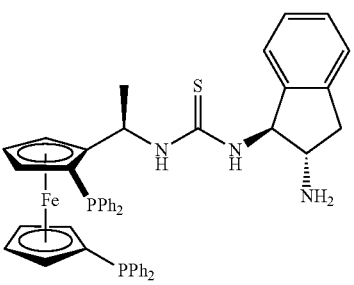

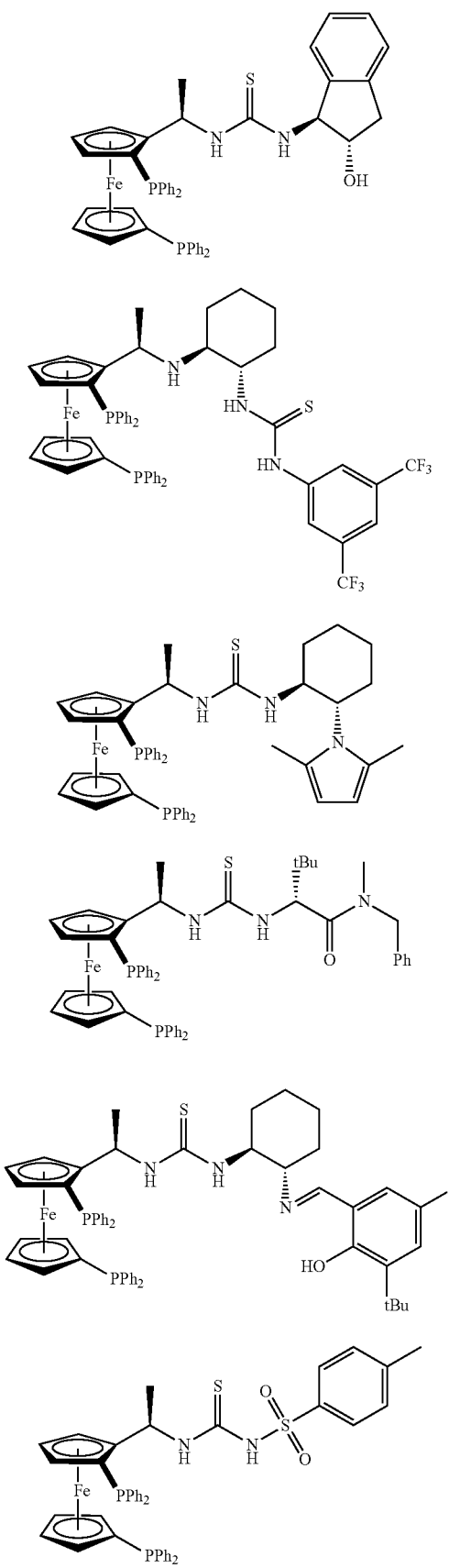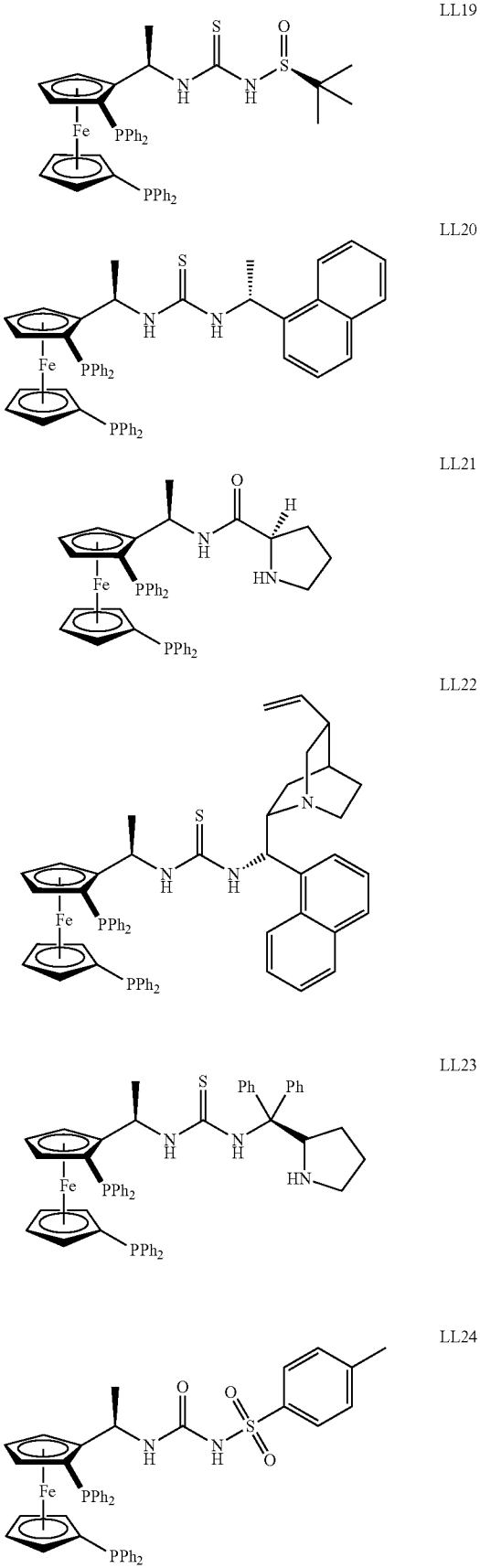

-continued
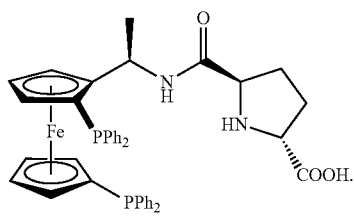
LL25
2. A ligand selected from the group consisting of compounds represented by the following formulae:
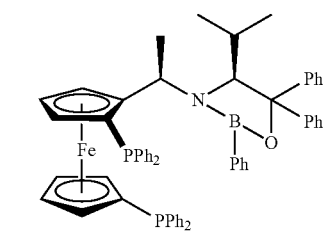
LL26
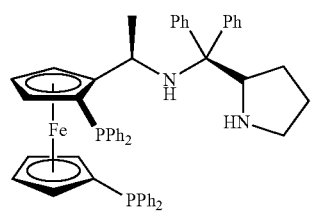
LL28
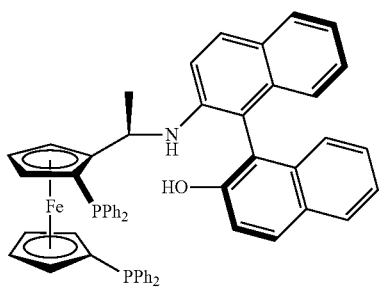
LL29
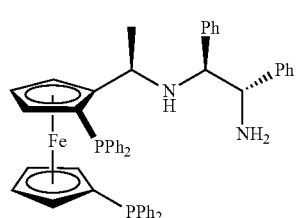
LL30
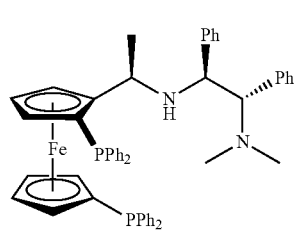
LL31
-continued
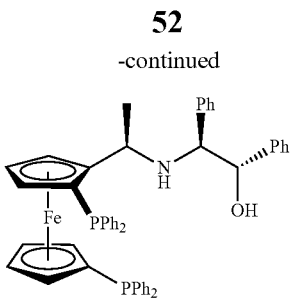
LL32
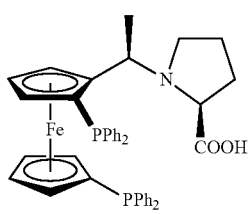
LL34
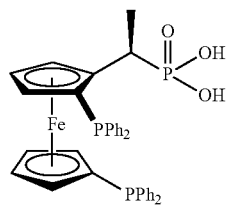
LL36
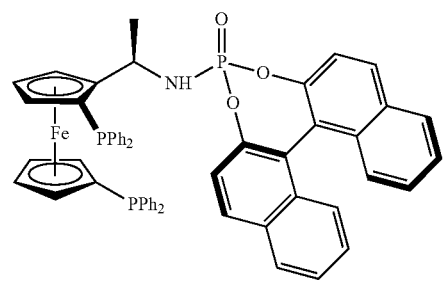
LL37
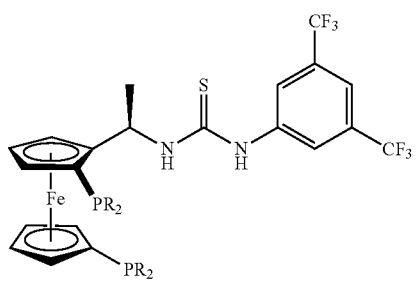
LL39
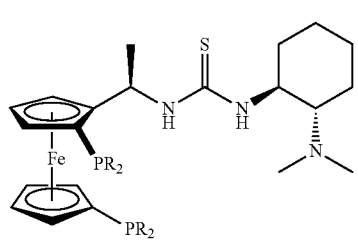
LL40

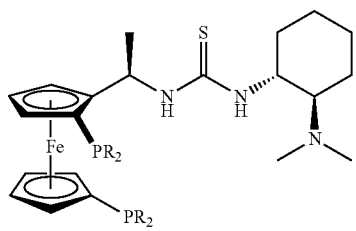
LL41
wherein R in the moiety —PR$_2$ is selected from the group consisting of phenyl; 4-CH$_3$-phenyl; 3,5-(CH$_3$)$_2$-phenyl; 3,5-(t-butyl)$_2$-phenyl; 3,5-(CF$_3$)$_2$-phenyl; 2-CH$_3$-phenyl; C$_6$F$_5$; 2-naphthyl; 1-naphthyl; t-butyl; i-propyl; cyclohexyl and cyclopentyl.
\* \* \* \* \*

UNITED STATES PATENT AND TRADEMARK OFFICE
CERTIFICATE OF CORRECTION

| | | |
|---|---|---|
| PATENT NO. | : 9,744,528 B2 | Page 1 of 1 |
| APPLICATION NO. | : 14/775159 | |
| DATED | : August 29, 2017 | |
| INVENTOR(S) | : Zhang | |

It is certified that error appears in the above-identified patent and that said Letters Patent is hereby corrected as shown below:

In the Specification

At Column 1, Line number 15, enter the following:
STATEMENT REGARDING FEDERALLY SPONSORED RESEARCH
This invention was made with government support under grant number GM058832 awarded by the National Institutes of Health. The government has certain rights in the invention.

Signed and Sealed this
Twenty-second Day of February, 2022

Drew Hirshfeld
*Performing the Functions and Duties of the*
*Under Secretary of Commerce for Intellectual Property and*
*Director of the United States Patent and Trademark Office*